United States Patent
Shin et al.

(10) Patent No.: US 10,651,397 B2
(45) Date of Patent: May 12, 2020

(54) ORGANIC LIGHT EMITTING COMPOUND AND ORGANIC LIGHT EMITTING DEVICE COMPRISING THE SAME

(71) Applicant: SFC CO., LTD., Chungcheonbuk-do (KR)

(72) Inventors: Bong-ki Shin, Jeongeup-si (KR); Bu-Bae Park, Daegu (KR); Ji-hee Park, Changwon-si (KR); Bong-hyang Lee, Busan (KR); Kyung-Hwa Park, Chuncheon-si (KR)

(73) Assignee: SFC CO., LTD., Cheongju-si (KR)

( * ) Notice: Subject to any disclaimer, the term of this patent is extended or adjusted under 35 U.S.C. 154(b) by 0 days.

(21) Appl. No.: 15/028,181

(22) PCT Filed: Oct. 10, 2014

(86) PCT No.: PCT/KR2014/009504
§ 371 (c)(1),
(2) Date: Apr. 8, 2016

(87) PCT Pub. No.: WO2015/053572
PCT Pub. Date: Apr. 16, 2015

(65) Prior Publication Data
US 2016/0248024 A1    Aug. 25, 2016

(30) Foreign Application Priority Data
Oct. 11, 2013    (KR) .................. 10-2013-0120939

(51) Int. Cl.
*H01L 51/00*    (2006.01)
*C07D 403/04*    (2006.01)
(Continued)

(52) U.S. Cl.
CPC ........ *H01L 51/0072* (2013.01); *C07D 401/14* (2013.01); *C07D 403/04* (2013.01);
(Continued)

(58) Field of Classification Search
CPC ... H01L 51/0071–51/0072; H01L 51/50–5096
See application file for complete search history.

(56) References Cited

U.S. PATENT DOCUMENTS

2005/0142379 A1* 6/2005 Juni ...................... G02B 5/0242
428/690
2012/0217485 A1* 8/2012 Lee ...................... G02B 5/0242
428/690
(Continued)

FOREIGN PATENT DOCUMENTS

CN    105339365 A    2/2016
JP    2003-045662 A    2/2003
(Continued)

OTHER PUBLICATIONS

Machine Translation of KR 2012/0117693 A.*
(Continued)

*Primary Examiner* — William E McClain
(74) *Attorney, Agent, or Firm* — NSIP Law

(57) ABSTRACT

The present invention relates to an organic light emitting compound and an organic light emitting device comprising the same, and the organic light emitting device employing the organic light emitting compound according to the present invention can be driven at a lower voltage than existing devices employing a phosphorescent host material, and has excellent power efficiency, improved light emission efficiency, and long lifespan characteristics.

12 Claims, 1 Drawing Sheet

(51) Int. Cl.
| | |
|---|---|
| *C09K 11/06* | (2006.01) |
| *C07D 405/14* | (2006.01) |
| *C07D 403/14* | (2006.01) |
| *C07D 409/14* | (2006.01) |
| *C07D 495/04* | (2006.01) |
| *C07D 401/14* | (2006.01) |
| *C07D 471/04* | (2006.01) |
| *C07F 7/08* | (2006.01) |
| *C07D 403/06* | (2006.01) |
| *C07F 5/02* | (2006.01) |
| *C07D 403/10* | (2006.01) |
| *C09K 11/02* | (2006.01) |
| *H01L 51/50* | (2006.01) |

(52) U.S. Cl.
CPC ......... *C07D 403/06* (2013.01); *C07D 403/10* (2013.01); *C07D 403/14* (2013.01); *C07D 405/14* (2013.01); *C07D 409/14* (2013.01); *C07D 471/04* (2013.01); *C07D 495/04* (2013.01); *C07F 5/025* (2013.01); *C07F 7/0814* (2013.01); *C09K 11/025* (2013.01); *C09K 11/06* (2013.01); *H01L 51/0052* (2013.01); *H01L 51/0058* (2013.01); *H01L 51/0059* (2013.01); *H01L 51/0067* (2013.01); *H01L 51/0073* (2013.01); *H01L 51/0074* (2013.01); *H01L 51/0085* (2013.01); *H01L 51/0094* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0071* (2013.01); *H01L 51/504* (2013.01); *H01L 51/5012* (2013.01); *H01L 51/5016* (2013.01); *H01L 2251/308* (2013.01)

(56) References Cited

U.S. PATENT DOCUMENTS

| | | | | |
|---|---|---|---|---|
| 2012/0248971 | A1* | 10/2012 | Okuyama | C09K 11/06 313/504 |
| 2014/0209880 | A1* | 7/2014 | Choi | H01L 51/0067 257/40 |
| 2015/0001489 | A1* | 1/2015 | Lee | H01L 51/0054 257/40 |
| 2016/0172604 | A1 | 6/2016 | Ikeda et al. | |
| 2016/0190477 | A1* | 6/2016 | Kawakami | C09K 11/06 257/40 |

FOREIGN PATENT DOCUMENTS

| | | | | |
|---|---|---|---|---|
| JP | 2003-133075 A | | 5/2003 | |
| JP | 2004-031004 A | | 1/2004 | |
| JP | 2008-214244 A | | 9/2008 | |
| JP | 2009246097 A | * | 10/2009 | |
| KR | 10-2011-0013220 A | | 2/2011 | |
| KR | 20120072784 A | * | 7/2012 | |
| KR | 10-2012-0117693 A | | 10/2012 | |
| WO | WO 2006-049013 A1 | | 5/2006 | |
| WO | WO-2010114264 A2 | * | 10/2010 | C09K 11/06 |

OTHER PUBLICATIONS

English Translations of International Search Report and Written Opinion for International Application No. PCT/KR2014/009504, dated Jan. 13, 2015, 11 pages.

* cited by examiner

| |
|---|
| 80 |
| 70 |
| 60 |
| 50 |
| 40 |
| 30 |
| 20 |
| 10 |

ORGANIC LIGHT EMITTING COMPOUND AND ORGANIC LIGHT EMITTING DEVICE COMPRISING THE SAME

CROSS-REFERENCE TO RELATED APPLICATIONS

This application is a national stage application filed under 35 U.S.C. 371 of International Application No. PCT/KR2014/009504, filed Oct. 10, 2014, which claims priority from Korean Patent Application No. KR 10-2013-0120939, filed Oct. 11, 2013, each of which is incorporated by reference herein in its entirety.

TECHNICAL FIELD

The present invention relates to organic light emitting compounds and organic electroluminescence devices including the same.

BACKGROUND ART

Organic electroluminescence devices are devices in which when charges are injected into an organic light emitting layer disposed between an electron injecting electrode (cathode) and a hole injecting electrode (anode), electrons and holes combine with each other in the light emitting layer and then the electron-hole pairs decay to emit light. Organic electroluminescence devices can be fabricated even on flexible transparent substrates, such as plastic substrates. Other advantages of organic electroluminescence devices are low driving voltages of 10 V or less, relatively low power consumption, and accurate color representation compared to plasma display panels and inorganic electroluminescence displays. In addition, organic electroluminescence devices can represent green, blue, and red colors. Due to these advantages, organic electroluminescence devices have been the subject of intense interest as next-generation full-color display devices.

Luminescent materials are the most important factors determining the luminous efficiency of organic electroluminescence devices. Fluorescent materials are widely used at present as luminescent materials but the development of phosphorescent materials is theoretically considered an approach to further improve the luminous efficiency of organic electroluminescence devices in view of the mechanism of light emission. Thus, various phosphorescent materials have been developed and are currently being developed. Particularly, 4,4'-N,N'-dicarbazolebiphenyl (CBP) is most widely known as a phosphorescent host material. Organic electroluminescence devices are known that use, as hosts, carbazole compounds whose carbazole skeletons are substituted with various groups (Japanese Patent Publication Nos. 2008-214244 and 2003-133075) or BAlq derivatives.

Organic electroluminescence devices using phosphorescent materials have considerably high current efficiency compared to devices using fluorescent materials. However, organic electroluminescence devices using BAlq and CBP as phosphorescent host materials do not offer significant advantages in terms of power efficiency over devices using fluorescent materials because of their higher driving voltages and do not reach a satisfactory level in terms of device life. Under these circumstances, there is a need to develop a more stable high-performance host material.

DETAILED DESCRIPTION OF THE INVENTION

Problems to be Solved by the Invention

Therefore, the present invention is intended to provide organic light emitting compounds that have improved power efficiency and life characteristics as well as high luminous efficiency compared to conventional luminescent materials. The present invention is also intended to provide organic electroluminescence devices that employ the organic light emitting compounds as luminescent materials, achieving low-voltage driving, high efficiency, and improved life characteristics.

Means for Solving the Problems

Aspects of the present invention provide organic light emitting compounds represented by Formula 1:

[Formula 1]

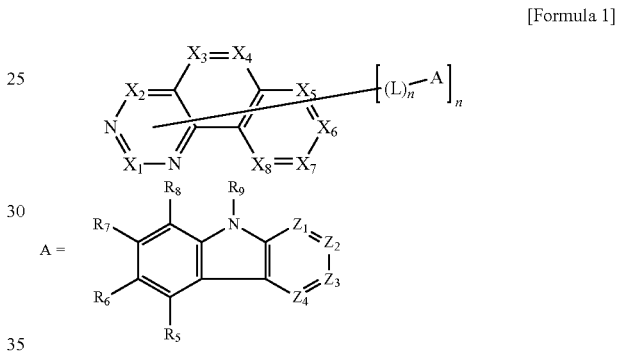

wherein $X_1$ to $X_8$, L, m, n, $R_5$ to $R_9$, and $Z_1$ to $Z_4$ are as defined below, and an organic electroluminescence device including at least one of the organic light emitting compounds.

Effects of the Invention

The organic electroluminescence devices employing the organic light emitting compounds according to the present invention can be driven at low voltages compared to conventional devices employing phosphorescent host materials. The low-voltage driving leads to high power efficiency while at the same time achieving improved luminous efficiency and life characteristics. Due to these advantages, the organic electroluminescence devices of the present invention are suitable for use in various displays and white lighting systems.

BRIEF DESCRIPTION OF THE DRAWINGS

FIG. 1 is a conceptual view illustrating a multilayer organic electroluminescence device according to one embodiment of the present invention.

BEST MODE FOR CARRYING OUT THE INVENTION

The present invention will now be described in more detail.

One aspect of the present invention is directed to organic light emitting compounds represented by Formula 1:

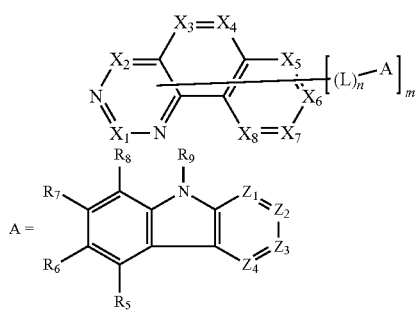

[Formula 1]

wherein $X_1$ to $X_8$ are identical to or different from each other and are each independently N or $CR_o$, provided that when $CR_o$ exists in plurality, the $CR_o$ groups may be identical to or different from each other, $Z_1$ to $Z_4$ are each independently N or are $CR_1$ to $CR_4$, respectively, L represents a linker and is a single bond or is selected from substituted or unsubstituted $C_1$-$C_{60}$ alkylene groups, substituted or unsubstituted $C_2$-$C_{60}$ alkenylene groups, substituted or unsubstituted $C_2$-$C_{60}$ alkynylene groups, substituted or unsubstituted $C_3$-$C_{60}$ cycloalkylene groups, substituted or unsubstituted $C_2$-$C_{60}$ heterocycloalkylene groups, substituted or unsubstituted $C_5$-$C_{60}$ arylene groups, and substituted or unsubstituted $C_2$-$C_{60}$ heteroarylene groups, n is an integer from 1 to 3, provided that when n is equal to or greater than 2, the plurality of L groups are identical to or different from each other, $R_o$ and $R_1$ to $R_9$ are identical to or different from each other and are each independently selected from a hydrogen atom, a deuterium atom, substituted or unsubstituted $C_1$-$C_{30}$ alkyl groups, substituted or unsubstituted $C_6$-$C_{40}$ aryl groups, substituted or unsubstituted $C_2$-$C_{30}$ heteroaryl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted $C_3$-$C_{60}$ cycloalkyl groups, substituted or unsubstituted $C_5$-$C_{30}$ cycloalkenyl groups, substituted or unsubstituted $C_5$-$C_{60}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_5$-$C_{60}$ arylthio groups, —$SiR_{11}R_{12}R_{13}$, and —$NR_{14}R_{15}$, $R_{11}$ to $R_{15}$ are identical to or different from each other and are each independently selected from a hydrogen atom, a deuterium atom, substituted or unsubstituted $C_1$-$C_{30}$ alkyl groups, substituted or unsubstituted $C_6$-$C_{40}$ aryl groups, substituted or unsubstituted $C_2$-$C_{30}$ heteroaryl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted $C_3$-$C_{60}$ cycloalkyl groups, substituted or unsubstituted $C_5$-$C_{30}$ cycloalkenyl groups, substituted or unsubstituted $C_5$-$C_{60}$ aryloxy groups, substituted or unsubstituted $C_1$-$C_{30}$ alkylthioxy groups, substituted or unsubstituted $C_5$-$C_{30}$ arylthioxy groups, and substituted or unsubstituted $C_5$-$C_{60}$ arylthio groups, with the proviso that $R_o$, $R_1$ to $R_9$, and substituents thereof may be bonded together to form a saturated or unsaturated ring, and m is an integer from 1 to 3.

Any one of $R_1$ to $R_9$ in A may be linked and bonded to L. According to a preferred embodiment of the present invention, $R_9$ in A may be linked to L. In this embodiment, A may be represented by

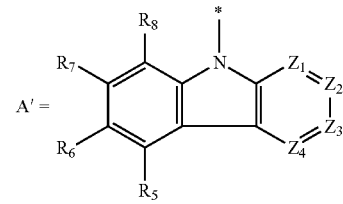

wherein $Z_1$ to $Z_4$ and $R_5$ to $R_8$ have the same meanings as $R_1$ to $R_9$ defined in Formula 1 and the asterisk (*) represents a site at which $R_9$ is bonded to L.

More specifically, A' may be selected from:

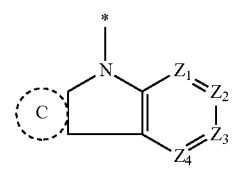

[Formula A1]

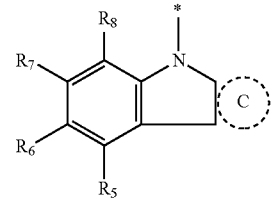

[Formula A2]

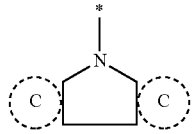

[Formula A3]

[Formula A4]

wherein $Z_1$ to $Z_4$ and $R_5$ to $R_8$ are as defined in Formula 1 and each

may be selected from, but not limited to:
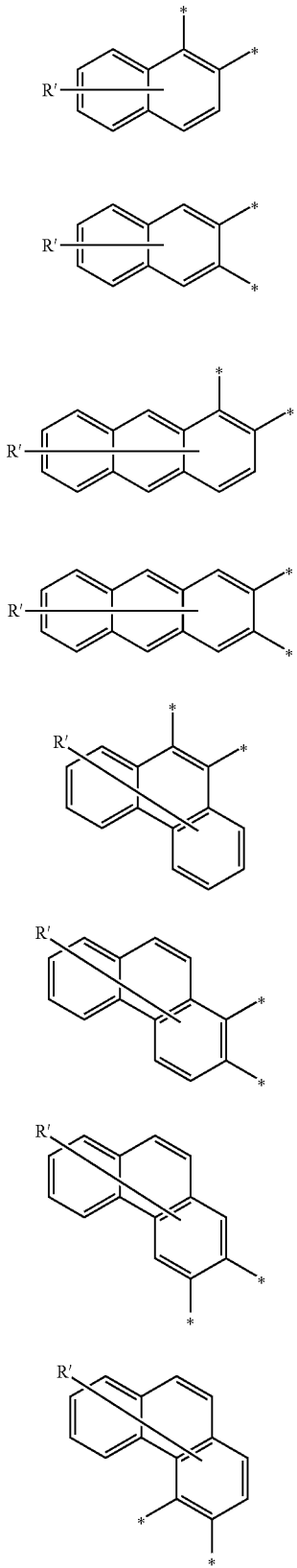
C1
C2
C3
C4
C5
C6
C7
C8
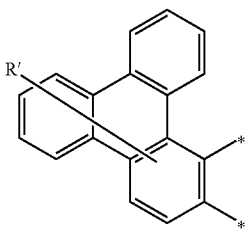
C9
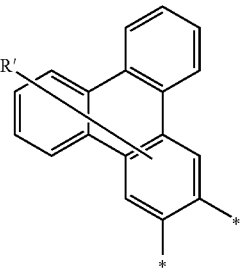
C10
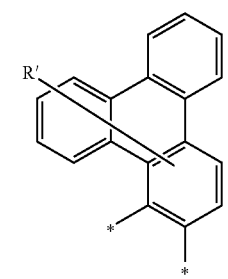
C11
wherein each asterisk (*) represents a bonding site and each R' has the same meaning as $R_1$ to $R_9$ defined in Formula 1.
More specifically, L may be a single bond or a linker selected from, but not limited to, the following structures:
[Structure B1]
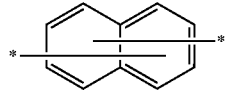
[Structure B2]
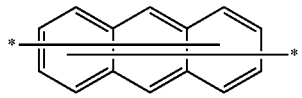
[Structure B3]
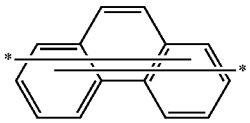
[Structure B4]

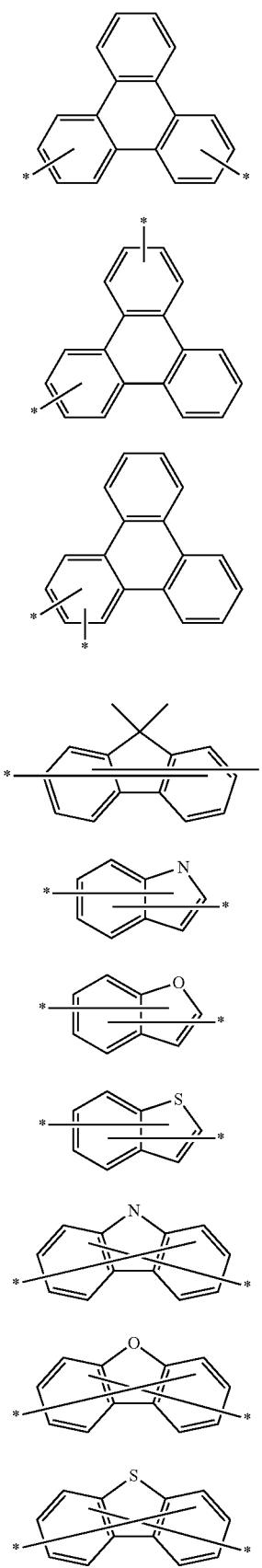
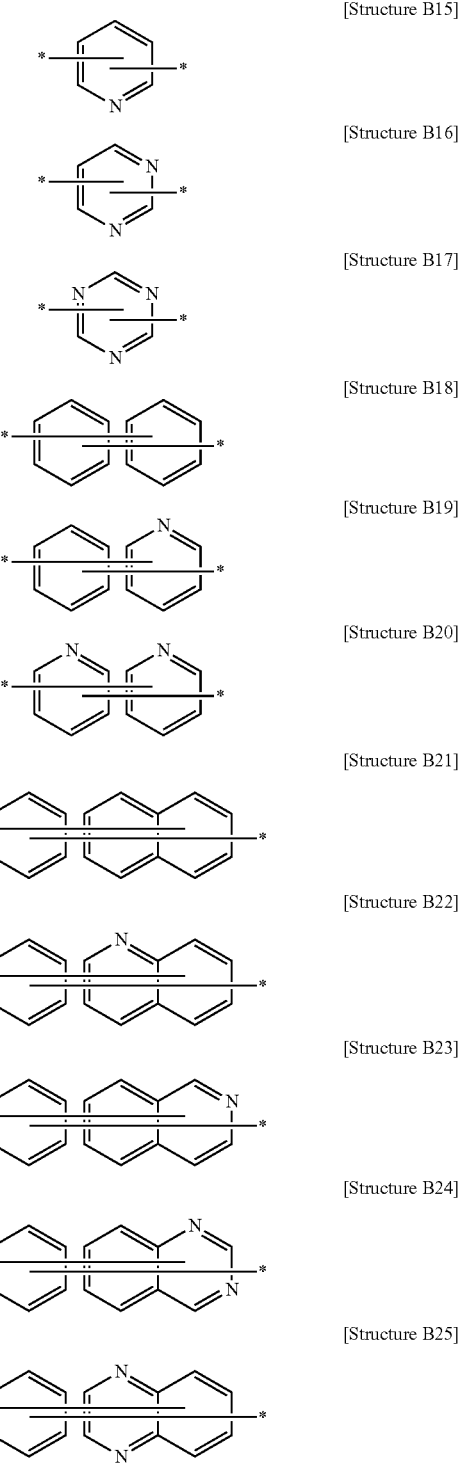
wherein hydrogen or deuterium atoms may be optionally bonded to the carbon atoms of the aromatic rings and R may optionally replace the nitrogen atoms, R having the same meaning as $R_1$ to $R_9$ defined in Formula 1.
The compounds of Formula 1 may vary in structure depending on the position where *-(L)$_n$-A is linked. The compounds of Formula 1 may be represented by Formula 1-1:

[Formula 1-1]

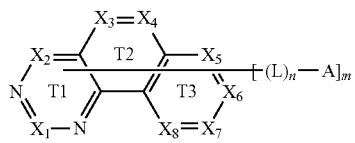

Specifically, the compounds of Formula 1 are represented by Formula 2 when *-(L)$_n$-A is linked to T1, Formula 3 when linked to T2, Formula 4 when linked to T1 and T2, Formula 5 when linked to T3, Formula 6 when linked to T2 and T3, Formula 7 when linked to T1 and T3 or Formula 8 when linked to T1, T2, and T3:

[Formula 2]

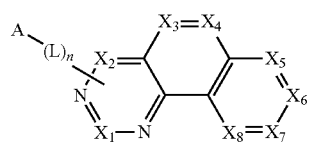

[Formula 3]

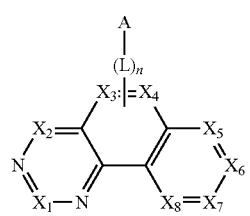

[Formula 4]

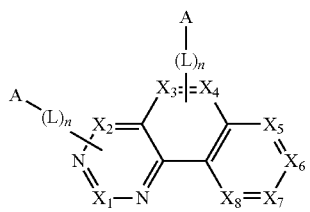

[Formula 5]

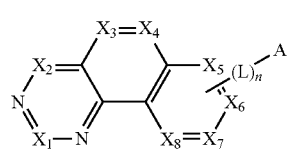

[Formula 6]

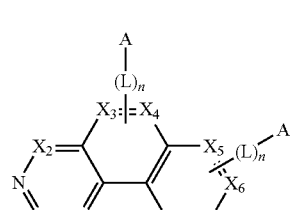

[Formula 7]

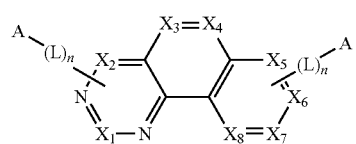

[Formula 8]

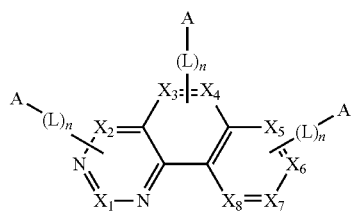

wherein L, $X_1$ to $X_8$, A, and n are as defined in Formula 1.

According to one preferred embodiment of the present invention, the organic light emitting compounds of Formula 1 may be more specifically selected from, but are not limited to, the following compounds 1 to 65:

[Compound 1]

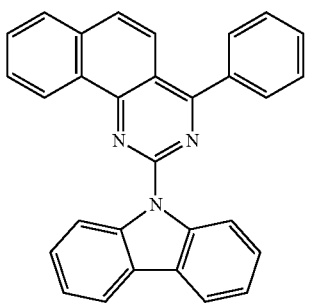

[Compound 2]

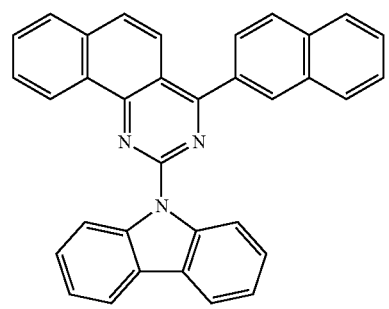

[Compound 3]

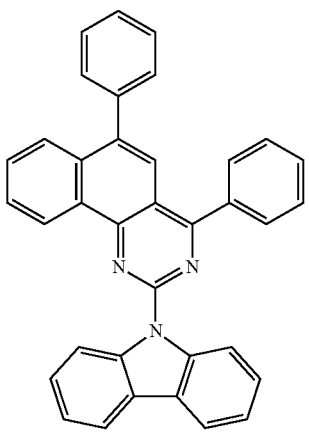

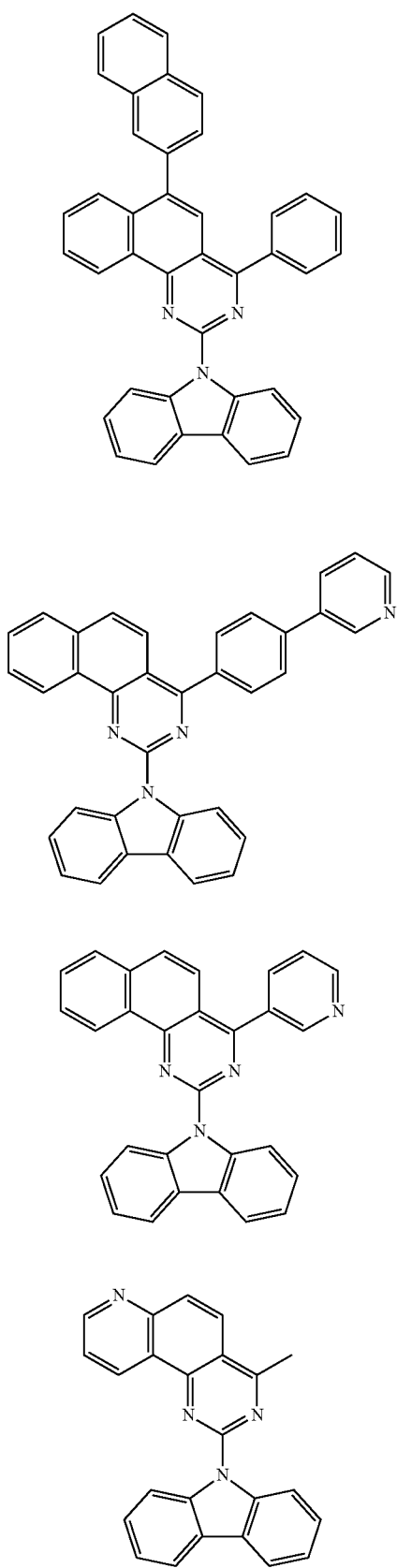
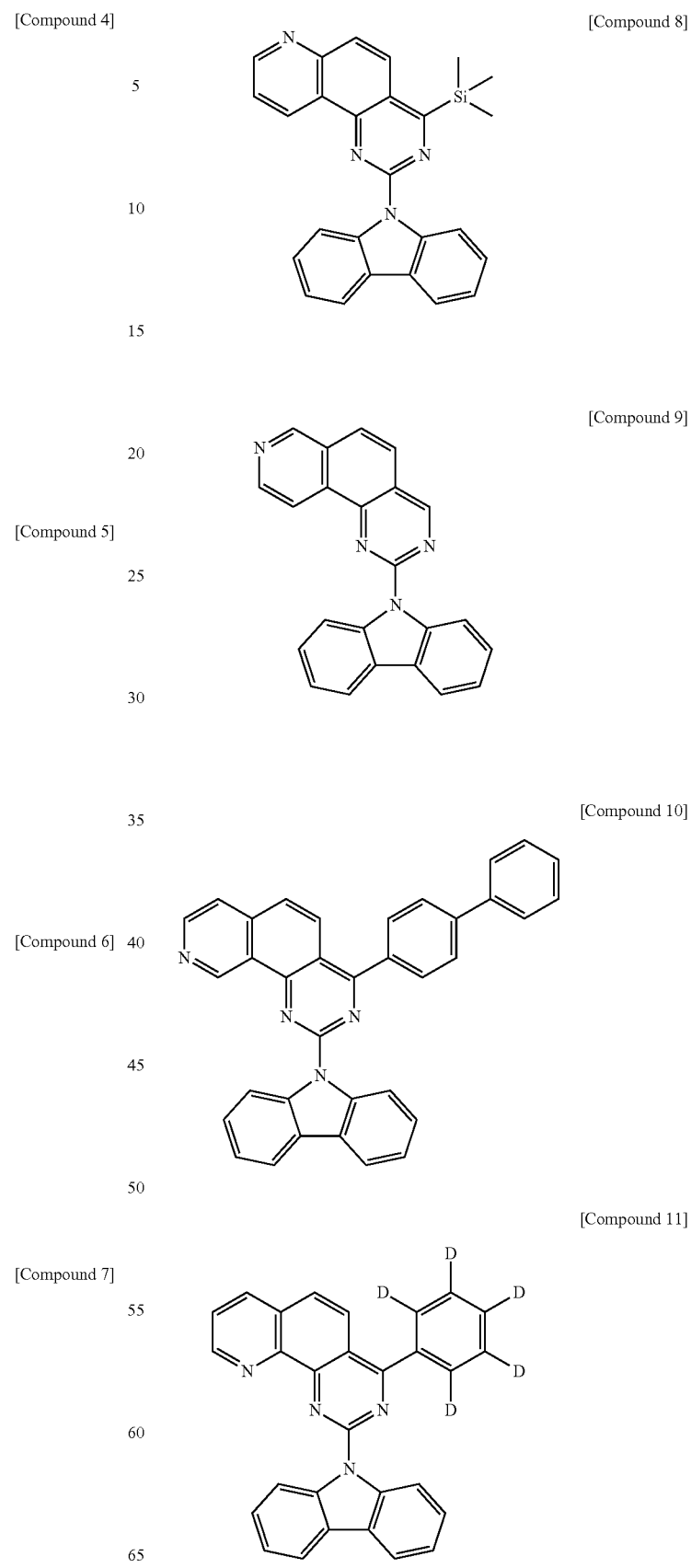

[Compound 12]
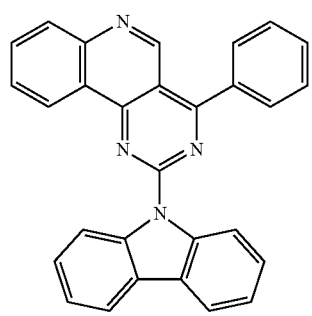
[Compound 13]
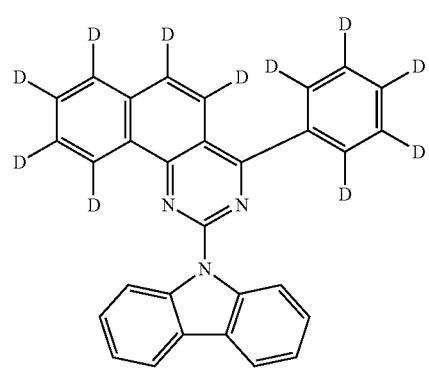
[Compound 14]
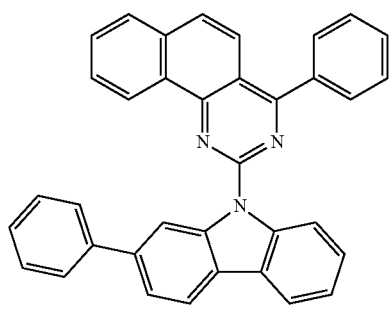
[Compound 15]
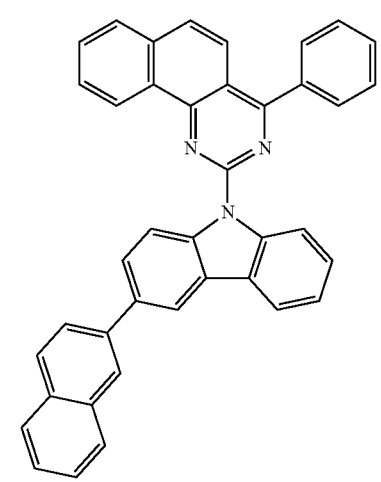
[Compound 16]
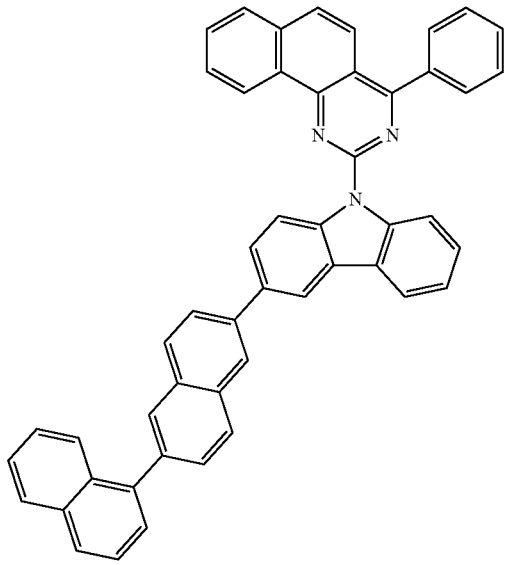
[Compound 17]
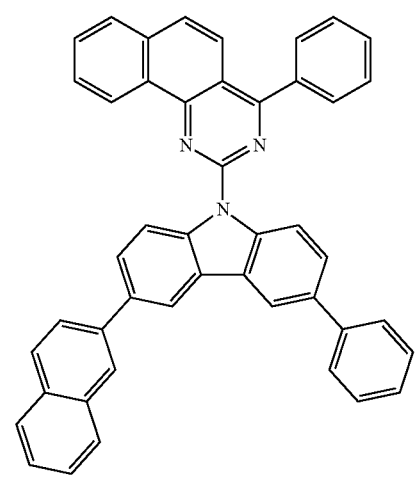
[Compound 18]
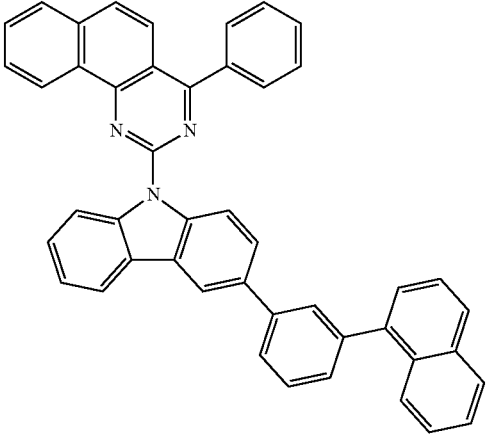

[Compound 19]
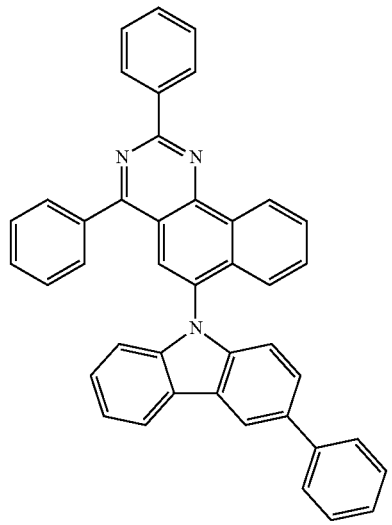
[Compound 21]
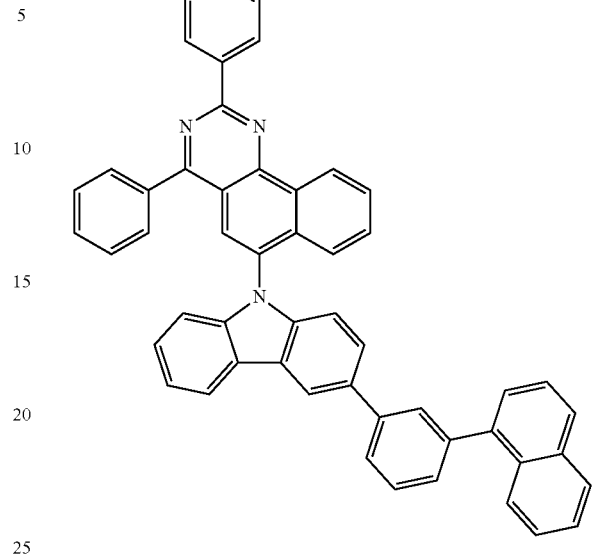
[Compound 20]
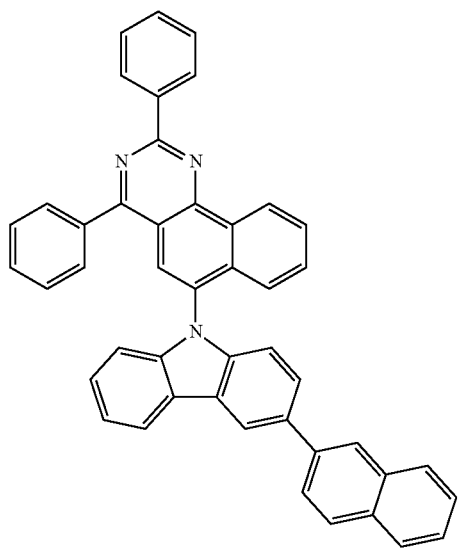
[Compound 22]
[Compound 23]

[Compound 24]
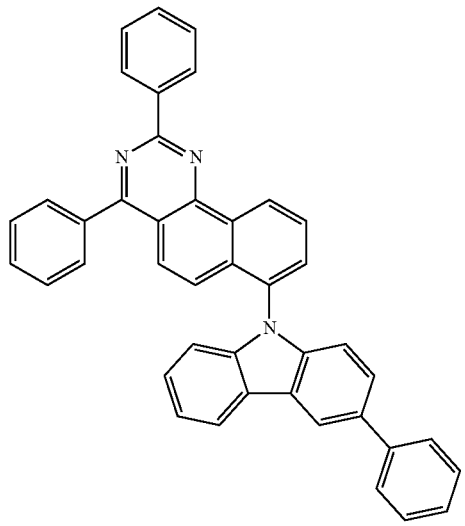
[Compound 25]
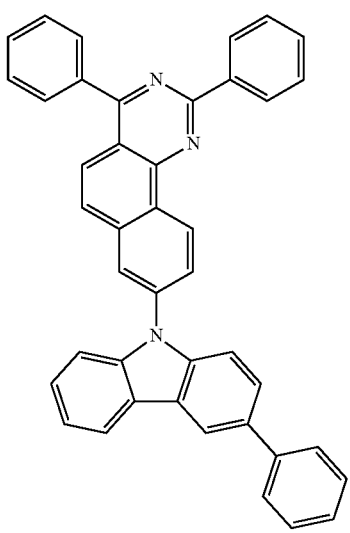
[Compound 26]
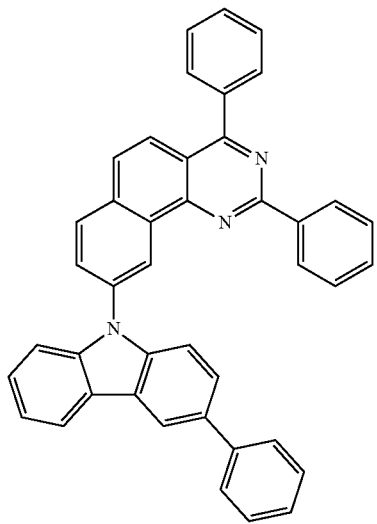
[Compound 27]
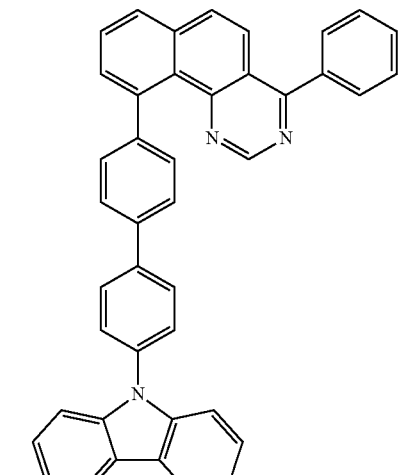
[Compound 28]
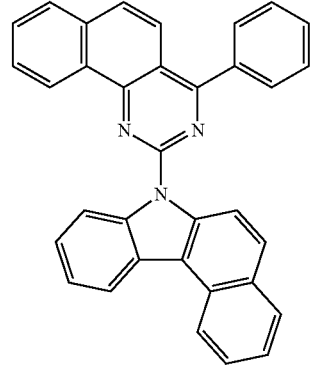
[Compound 29]
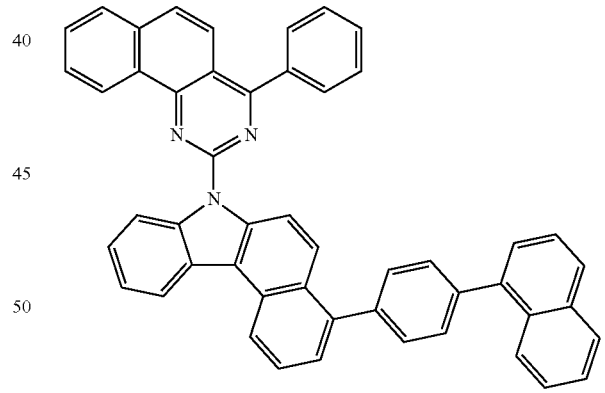
[Compound 30]
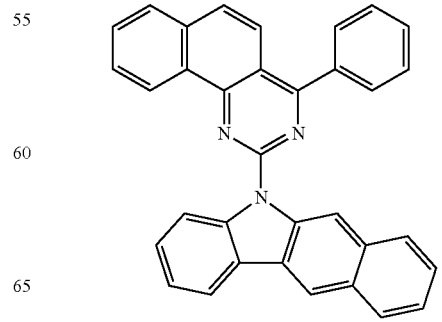

[Compound 31]
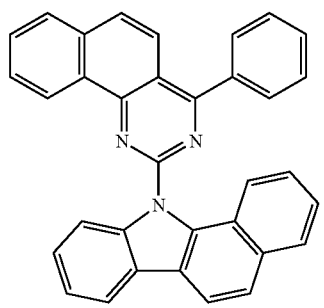
[Compound 32]
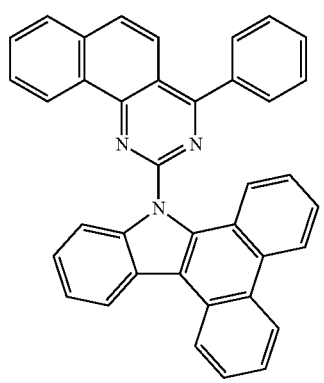
[Compound 33]
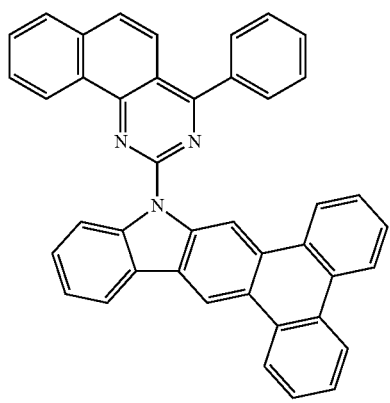
[Compound 34]
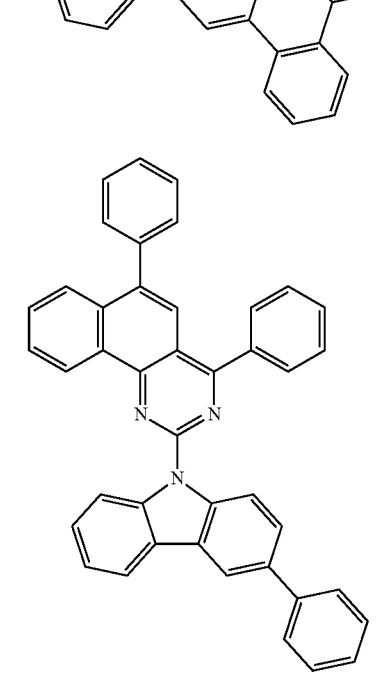
[Compound 35]
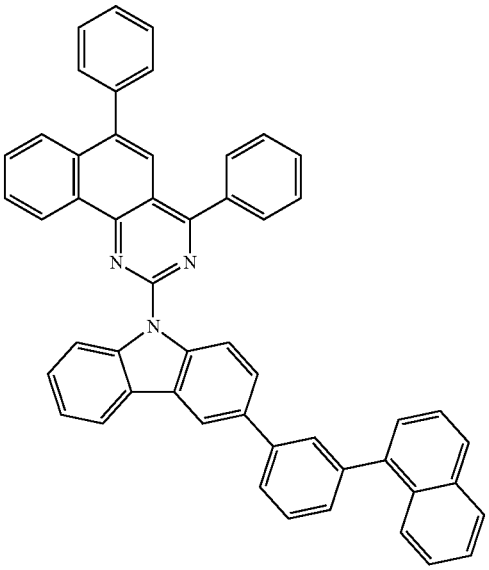
[Compound 36]
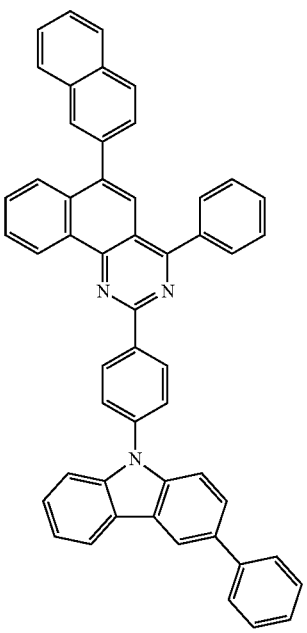

[Compound 37]
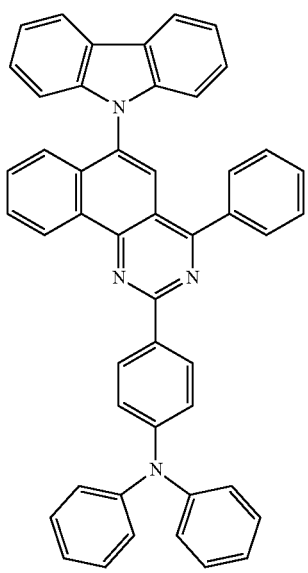
[Compound 38]
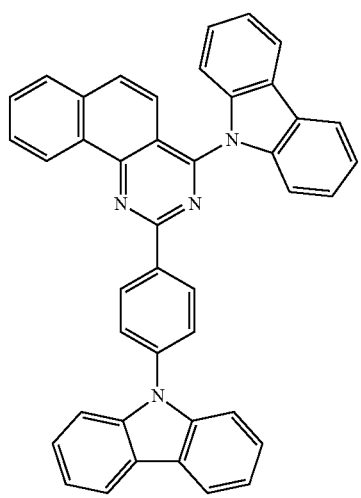
[Compound 39]
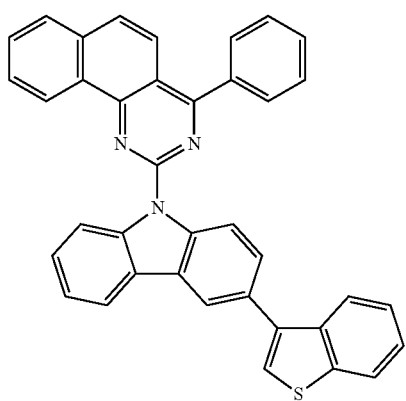
[Compound 40]
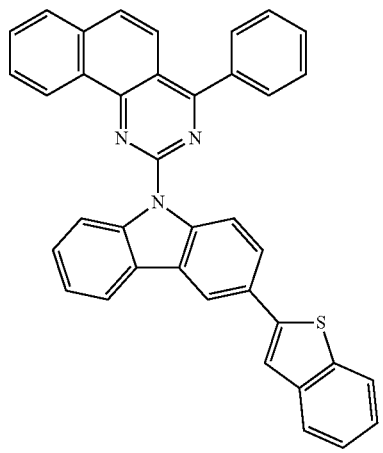
[Compound 41]
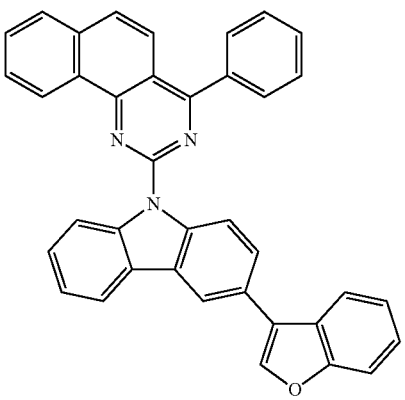
[Compound 42]
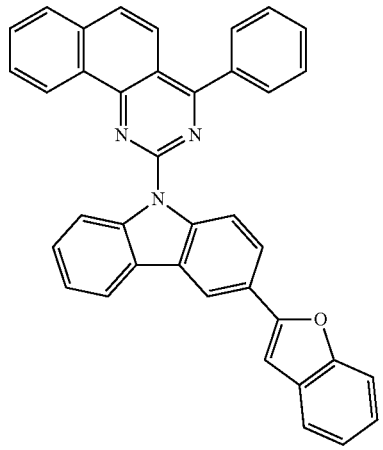

[Compound 43]
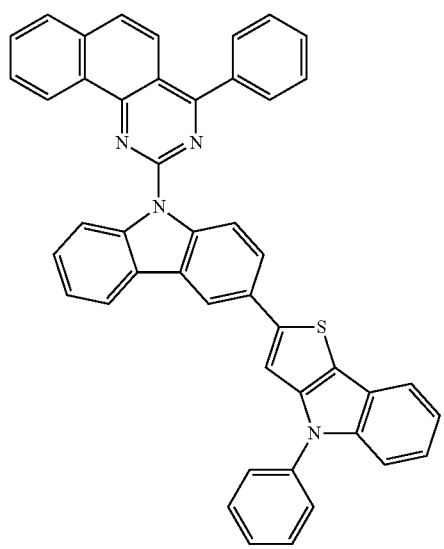
[Compound 44]
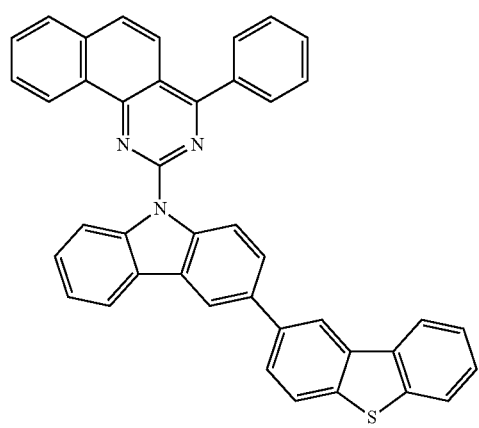
[Compound 45]
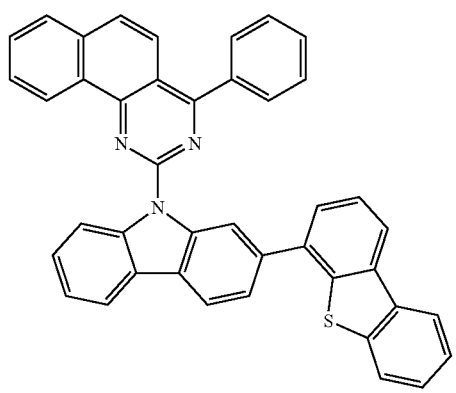
[Compound 46]
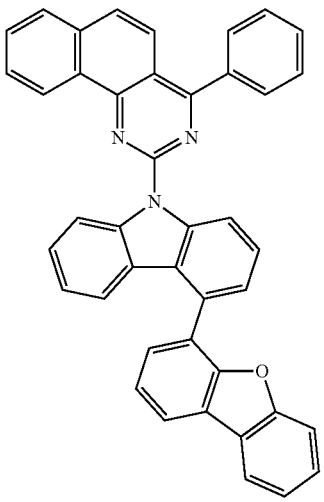
[Compound 47]
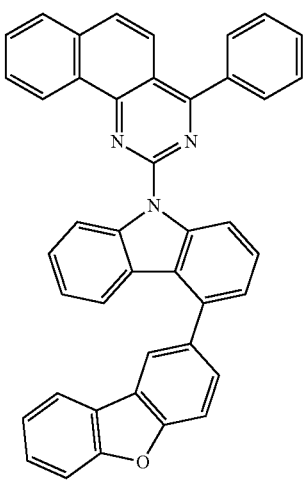
[Compound 48]
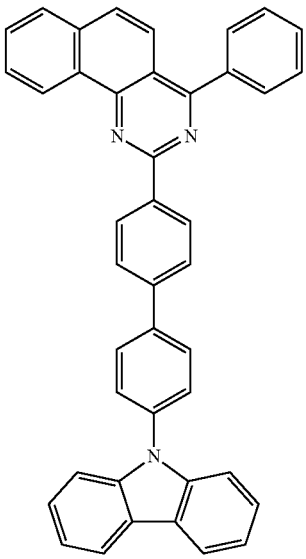

[Compound 49]
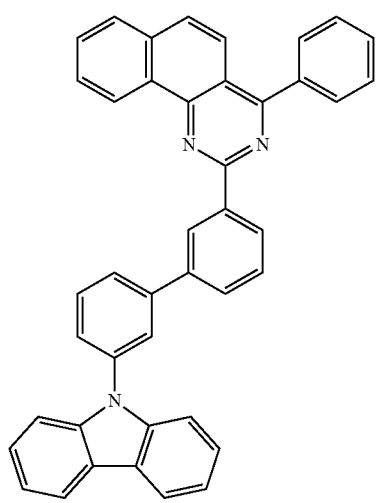
[Compound 51]
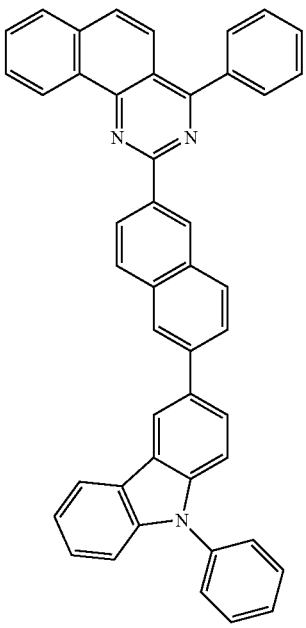
[Compound 50]
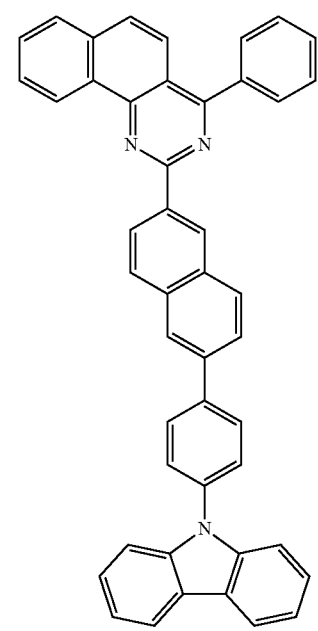
[Compound 52]
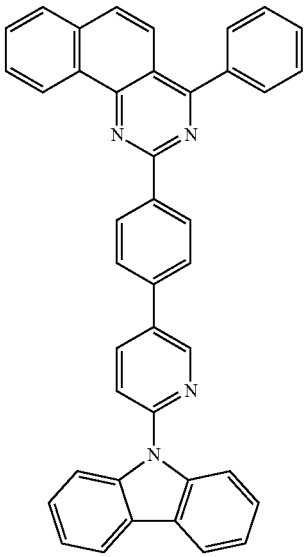

[Compound 53]
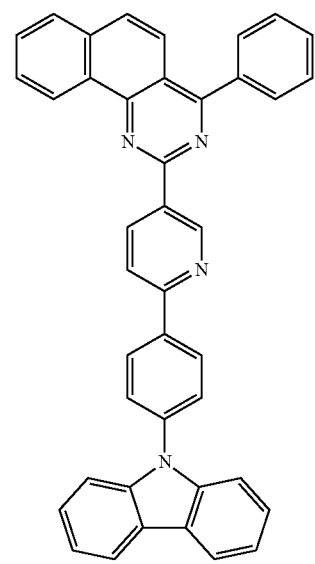
[Compound 54]
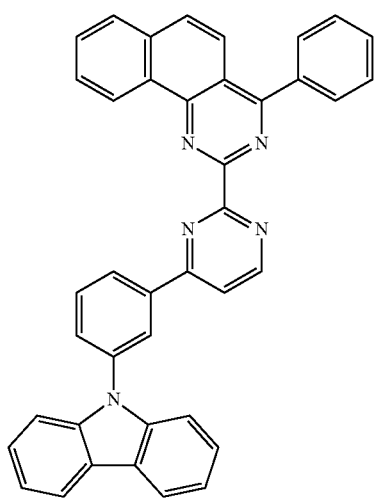
[Compound 55]
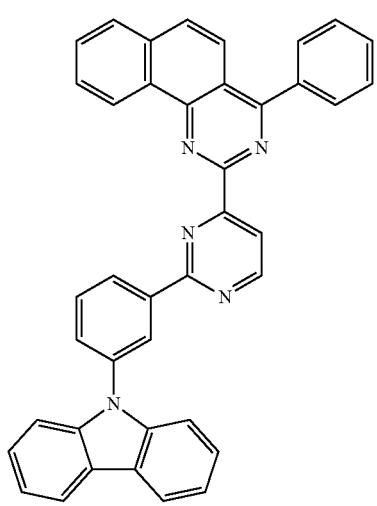
[Compound 56]
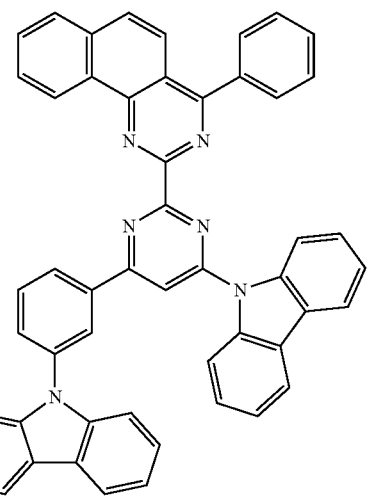
[Compound 57]
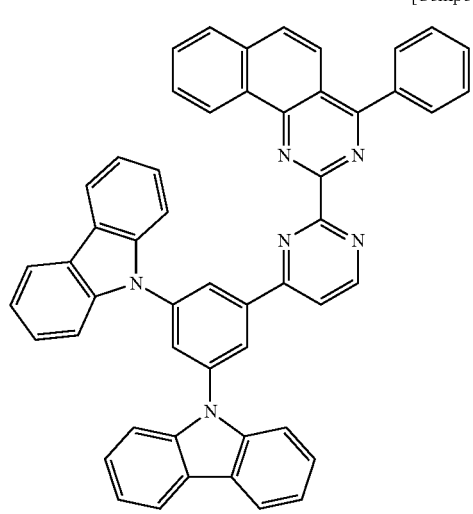
[Compound 58]
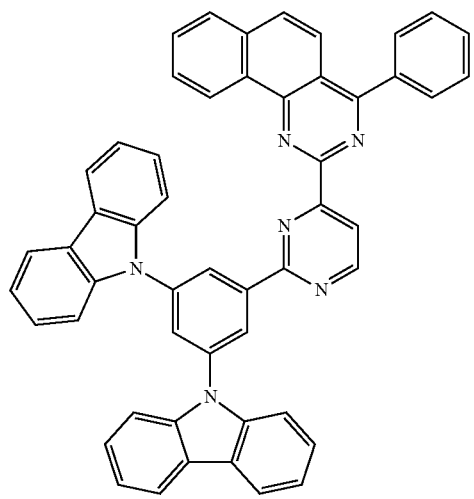

[Compound 59]
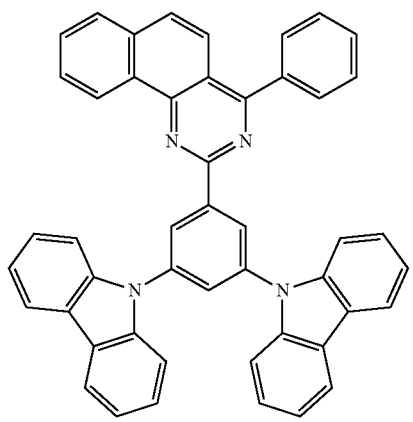
[Compound 60]
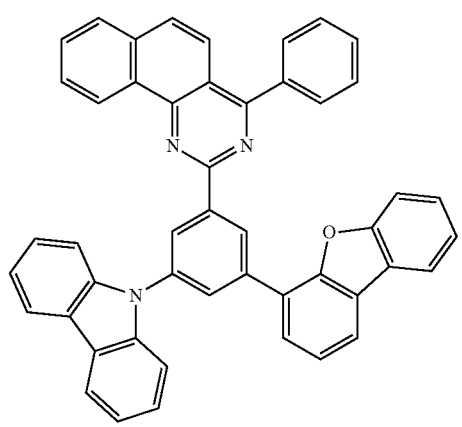
[Compound 61]
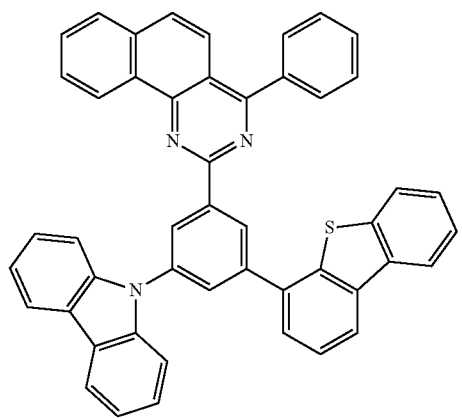
[Compound 62]
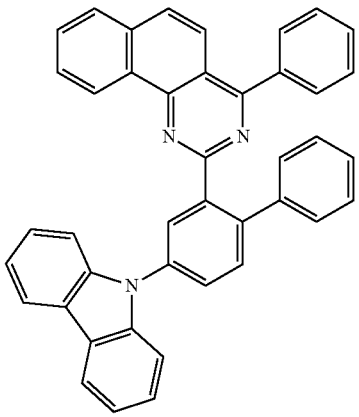
[Compound 63]
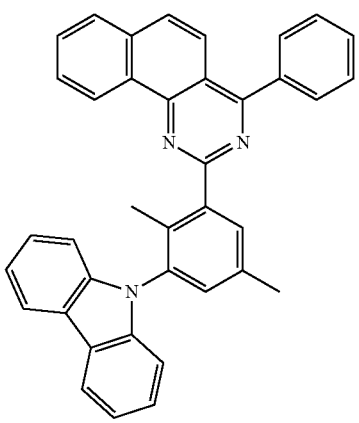
[Compound 64]
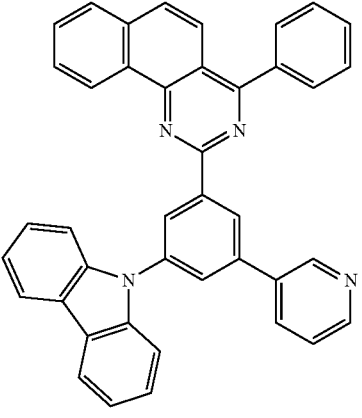

[Compound 65]

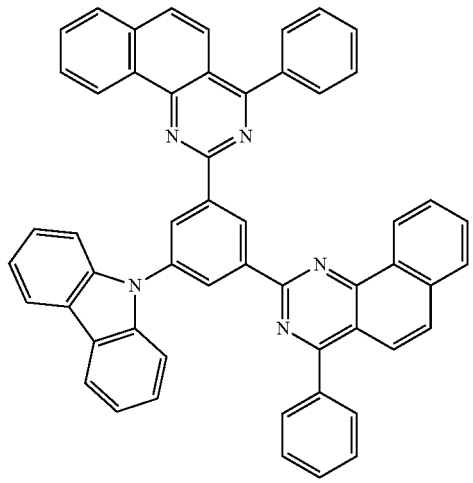

A further aspect of the present invention is directed to an organic electroluminescence device including a first electrode, a second electrode, and at least one organic layer interposed between the first and second electrodes wherein the organic layer includes at least one of the organic light emitting compounds represented by Formula 1.

The organic layer including the organic light emitting compound of the present invention may include at least one layer selected from a hole injecting layer, a hole transport layer, a functional layer having functions of both hole injection and hole transport, a light emitting layer, an electron transport layer, and an electron injecting layer.

The organic layer interposed between the first and second electrodes may include a light emitting layer. The light emitting layer may be composed of a host and a dopant. The organic light emitting compound of the present invention may be used as the host.

In the case where the light emitting layer includes a host and a dopant, the content of the dopant may be typically selected in the range of about 0.01 to about 20 parts by weight, based on 100 parts by weight the host.

Hereinafter, the organic electroluminescence device of the present invention will be explained in more detail with reference to FIG. 1.

FIG. 1 is a cross-sectional view illustrating the structure of an organic electroluminescence device according to one embodiment of the present invention. The organic electroluminescence device includes an anode 20, a hole transport layer 40, an organic light emitting layer 50, an electron transport layer 60, and a cathode 80. The organic electroluminescence device may optionally further include a hole injecting layer 30 and an electron injecting layer 70. In addition to these layers, one or more intermediate layers may be further formed in the organic electroluminescence device. A hole blocking layer or an electron blocking layer may be further formed in the organic electroluminescence device. The device may further include one or more organic layers with various functions depending on the desired characteristics thereof.

Referring to FIG. 1, a detailed description is given of the organic electroluminescence device and its fabrication method.

First, an electrode material for the anode 20 is coated on a substrate 10 to form the anode 20. The substrate 10 may be any of those used in general organic electroluminescence devices. The substrate 10 is preferably an organic substrate or a transparent plastic substrate that is excellent in transparency, surface smoothness, ease of handling, and waterproofness. A highly transparent and conductive metal oxide, such as indium tin oxide (ITO), indium zinc oxide (IZO), tin oxide ($SnO_2$) or zinc oxide (ZnO), is used as the anode material.

A material for the hole injecting layer 30 is coated on the anode 20 by vacuum thermal evaporation or spin coating to form the hole injecting layer 30. Then, a material for the hole transport layer 40 is coated on the hole injecting layer 30 by vacuum thermal evaporation or spin coating to form the hole transport layer 40.

The material for the hole injecting layer is not specially limited so long as it is commonly used in the art, and specific examples thereof include 4,4',4''-tris(2-naphthylphenyl-phenylamino)triphenylamine (2-TNATA), N,N'-di(1-naphthyl)-N,N'-diphenylbenzidine (NPD), N,N'-diphenyl-N,N'-bis(3-methylphenyl)-1,1'-biphenyl-4,4'-diamine (TPD), and N,N'-diphenyl-N,N'-bis[4-(phenyl-m-tolylamino)phenyl]biphenyl-4,4'-diamine (DNTPD).

The material for the hole transport layer is not specially limited so long as it is commonly used in the art, and examples thereof include N,N'-bis(3-methylphenyl)-N,N'-diphenyl-[1,1-biphenyl]-4,4'-diamine (TPD) and N,N'-di(naphthalen-1-yl)-N,N'-diphenylbenzidine (α-NPD).

Subsequently, the organic light emitting layer 50 is laminated on the hole transport layer 40. A hole blocking layer (not shown) may be optionally formed on the organic light emitting layer 50 by vacuum thermal evaporation or spin coating. The hole blocking layer blocks holes from entering the cathode through the organic light emitting layer. This role of the hole blocking layer prevents the life and efficiency of the device from deteriorating. A material having a very low highest occupied molecular orbital (HOMO) energy level is used for the hole blocking layer. The hole blocking material is not particularly limited so long as it has the ability to transport electrons and a higher ionization potential than the light emitting compound. Representative examples of suitable hole blocking materials include BAlq, BCP, and TPBI.

Examples of materials for the hole blocking layer include, but are not limited to, BAlq, BCP, Bphen, TPBI, NTAZ, $BeBq_2$, OXD-7, and Liq.

The electron transport layer 60 is deposited on the hole blocking layer by vacuum thermal evaporation or spin coating and the electron injecting layer 70 is formed thereon. A metal for the formation of the cathode is deposited on the electron injecting layer 70 by vacuum thermal evaporation to form the cathode 80, completing the fabrication of the organic EL device. As the metal for the formation of the cathode, there may be used, for example, lithium (Li), magnesium (Mg), aluminum (Al), aluminum-lithium (Al—Li), calcium (Ca), magnesium-indium (Mg—In) or magnesium-silver (Mg—Ag). The organic EL device may be of top emission type. In this case, a transmissive material, such as ITO or IZO, may be used to form the cathode.

The material for the electron transport layer functions to stably transport electrons injected from the electron injecting electrode (i.e. the cathode). The material for the electron transport layer may be any known electron transport material, and examples thereof include, but are not limited to, quinoline derivatives, particularly, tris(8-quinolinolate)aluminum ($Alq_3$), TAZ, Balq, $Bebq_2$, and AND. Oxadiazole derivatives, such as PBD, BMD, and BND, may also be used.

The organic light emitting layer of the organic electroluminescence device may further include one or more phosphorescent dopants, in addition to at least one of the organic light emitting compounds represented by Formula 1.

The phosphorescent dopants employed in the organic electroluminescence device may be, for example, copper, boron, and metal complexes. Examples of the metal complexes include, but are not limited to, iridium, platinum, palladium, and ruthenium complexes.

The light emitting layer may further include one or more phosphorescent host compounds, in addition to at least one of the organic light emitting compounds represented by Formula 1.

One or more layers selected from the hole injecting layer, the hole transport layer, the electron blocking layer, the light emitting layer, the hole blocking layer, the electron transport layer, and the electron injecting layer may be formed by a monomolecular deposition or solution process. According to the deposition process, the material for each layer is evaporated under heat and vacuum or reduced pressure to form the layer in the form of a thin film. According to the solution process, the material for each layer is mixed with a suitable solvent and the mixture is then formed into a thin film by a suitable method, such as ink-jet printing, roll-to-roll coating, screen printing, spray coating, dip coating or spin coating.

The organic electroluminescence device can be used in systems selected from flat panel displays, flexible displays, monochromatic flat panel lighting systems, white flat panel lighting systems, flexible monochromatic lighting systems, and flexible white lighting systems.

MODE FOR CARRYING OUT THE INVENTION

The present invention will be explained in more detail with reference to preferred embodiments in the following examples. However, it will be appreciated by those skilled in the art that these embodiments are provided for illustrative purposes only and are not intended to limit the scope of the invention.

Synthesis Example 1

Synthesis of Compound 39

[Reaction 1-1] Synthesis of Intermediate 1-a

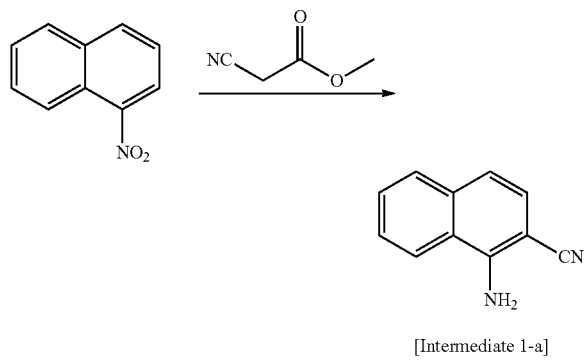

[Intermediate 1-a]

97 g (0.56 mol) of 1-nitronaphthalene, 166.5 g (1.68 mol) of methyl cyanoacetate, 40.1 g (0.62 mol) of potassium cyanide, and 62.9 g (1.12 mol) of potassium hydroxide were mixed and stirred. To the mixture was added 970 mL of dimethylformamide, followed by stirring at 60° C. overnight. The resulting mixture was concentrated under reduced pressure to remove the solvent, and then 500 mL of a 10% aqueous solution of sodium hydroxide was added thereto. The mixture was refluxed for about 1 h. The reaction mixture was extracted with ethyl acetate, separated by column chromatography, and recrystallized from toluene and heptane, affording 50.8 g of Intermediate 1-a (yield 54%).

[Reaction 1-2] Synthesis of Intermediate 1-b

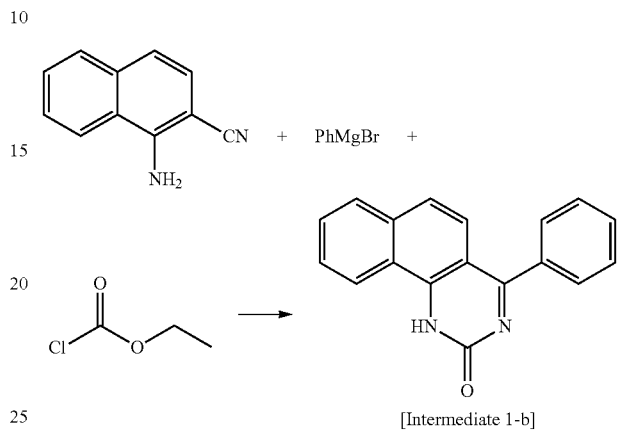

[Intermediate 1-b]

Intermediate 1-a (25.0 g, 149 mmol) synthesized in Reaction 1-1 was dissolved and stirred in 200 mL of tetrahydrofuran. The solution was cooled to 0° C. and then phenylmagnesium bromide (3.0 M in Et$_2$O) (87.4 mL, 297 mmol) was added dropwise thereto. The mixture was refluxed for 1 h. After cooling to 0° C., ethyl chloroformate (19.4 g, 179 mmol) was added dropwise. The resulting mixture was refluxed for 1 h. The reaction mixture was made weakly acidic by addition of a saturated aqueous ammonium chloride solution. The resulting solid was collected by filtration, affording 32.4 g of Intermediate 1-b (yield 80%).

[Reaction 1-3] Synthesis of Intermediate 1-c

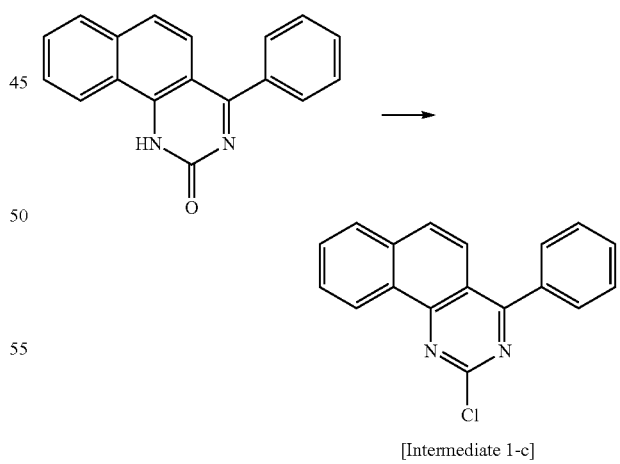

[Intermediate 1-c]

30.0 g (110 mmol) of Intermediate 1-b synthesized in Reaction 1-2 was refluxed in 80 mL of phosphorus oxychloride for 12 h. After cooling to −20° C., 400 mL of distilled water was added dropwise. The resulting solid was collected by filtration and recrystallized from toluene and heptane, affording 14.1 g of Intermediate 1-c (yield 44%).

[Reaction 1-4] Synthesis of Intermediate 1-d

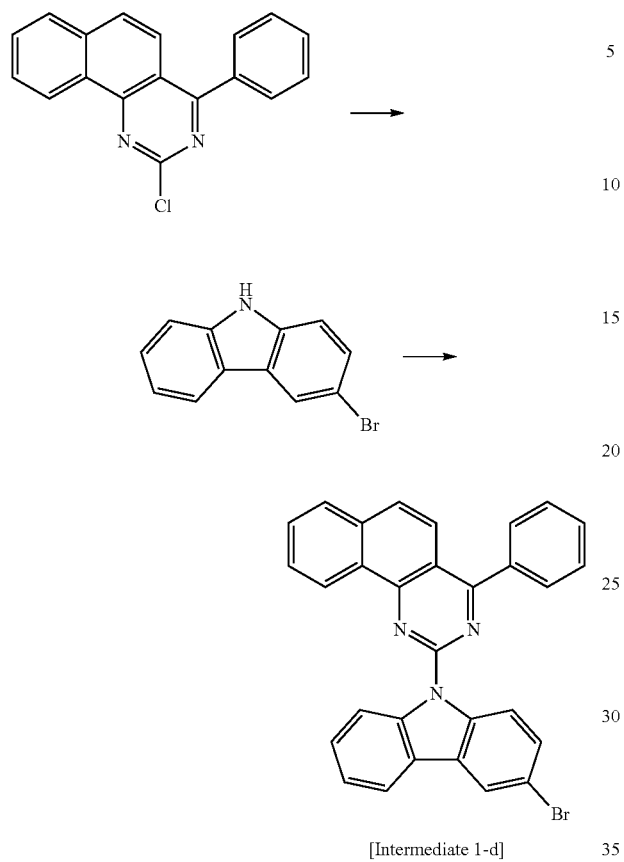

[Intermediate 1-d]

0.91 g (37 mmol) of 60% sodium hydride and 30 mL of dimethylformamide were mixed and cooled. To the mixture was added dropwise a solution of 6.0 g (24 mmol) of 3-bromo-9H-carbazole in 60 mL of dimethylformamide. The resulting mixture was stirred for 1 h. A solution of 9.2 g (32 mmol) of Intermediate 1-c synthesized in Reaction 1-3 in 60 mL of dimethylformamide was added dropwise. The mixture was allowed to warm to room temperature, followed by stirring for 2 h. 300 mL of distilled water was added to precipitate a solid. The solid was collected by filtration and recrystallized from toluene, affording 9.5 g of Intermediate 1-d (yield 78%).

[Reaction 1-5] Synthesis of Intermediate 1-e

[Intermediate 1-e]

50.0 g (0.235 mol) of 3-bromobenzothiophene, 71.5 g (0.282 mol) of bis(pinacolato)diboron, 5.2 g (0.007 mol) of $PdCl_2$ (dppf), 57.57 g (0.587 mol) of potassium acetate, and 500 ml of toluene were mixed and refluxed for 12 h. The reaction mixture was filtered at a high temperature and purified by column chromatography, affording 39.0 g of Intermediate 1-e (yield 64%).

[Reaction 1-6] Synthesis of Compound 39

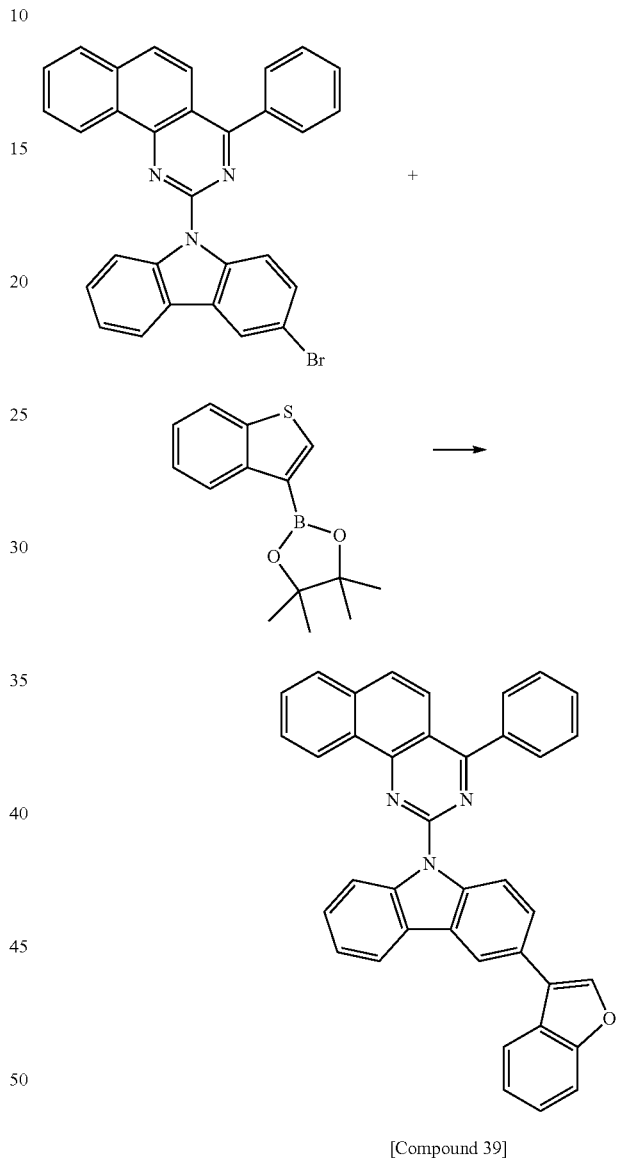

[Compound 39]

10.0 g (33 mmol) of Intermediate 1-d synthesized in Reaction 1-4, 10.4 g (40 mmol) of Intermediate 1-e synthesized in Reaction 1-5, 0.8 g (0.001 mmol) of tetrakis(triphenylphosphine)palladium, 13.8 g (100 mmol) of potassium carbonate, 40 mL of 1,4-dioxane, and 40 mL of toluene, and 14 mL of distilled water were mixed and refluxed for 12 h. After cooling to room temperature, the reaction mixture was extracted with ethyl acetate and purified by column chromatography, affording 13.0 g of Compound 39 (yield 70%).

MS: m/z 554

Synthesis Example 2

Synthesis of Compound 37

[Reaction 2-1] Synthesis of Intermediate 2-a

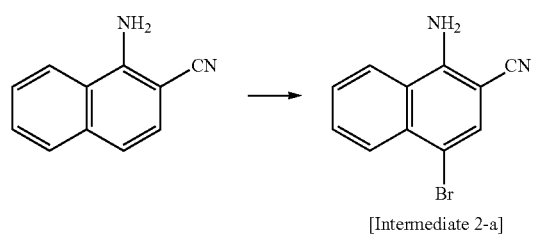

[Intermediate 2-a]

50.0 g (297 mmol) of Intermediate 1-a synthesized in Reaction 1-1 and 500 mL of dimethylformamide were mixed and cooled to 0° C. To the mixture was added dropwise 55.56 g (312 mmol) of N-bromosuccinimide. The resulting mixture was allowed to warm to room temperature, followed by stirring for 4 h. Distilled water was added dropwise to precipitate a solid. The solid was collected by filtration and purified by column chromatography, affording 68.0 g of Intermediate 2-a (yield 93%).

[Reaction 2-2] Synthesis of Intermediate 2-b

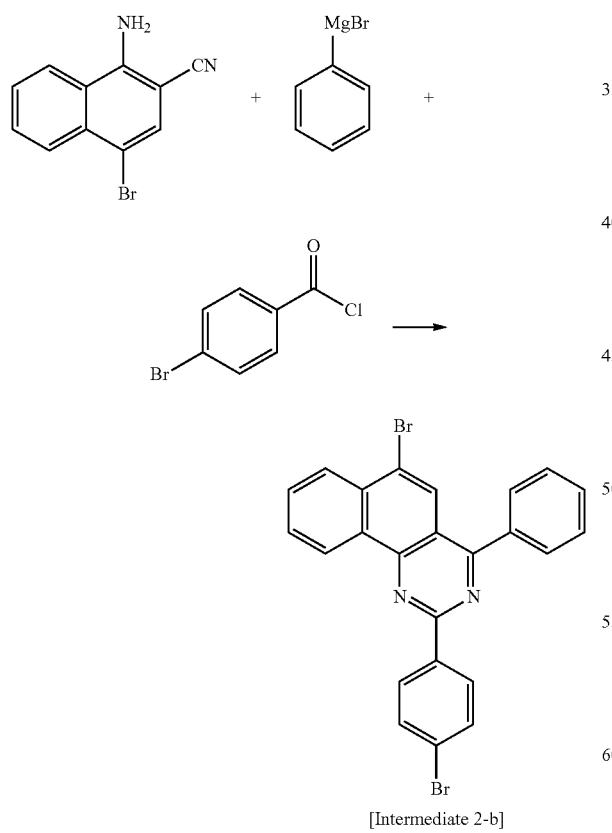

[Intermediate 2-b]

10.0 g (41 mmol) of Intermediate 2-a synthesized in Reaction 2-1 and 200 mL of tetrahydrofuran were mixed and 27.6 mL (83 mmol) of 3 M phenylmagnesium bromide was added dropwise thereto. The mixture was refluxed for 3 h. After cooling to 0° C., a solution of 10.8 g (0.571 mmol) of 4-bromobenzoyl chloride in 150 mL of tetrahydrofuran was added dropwise. The resulting mixture was refluxed for 2 h. The reaction mixture was cooled to 0° C., added with a saturated aqueous solution of ammonium chloride, extracted with ethyl acetate and purified by column chromatography, affording 12.0 g of Intermediate 2-b (yield 58%).

[Reaction 2-3] Synthesis of Compound 37

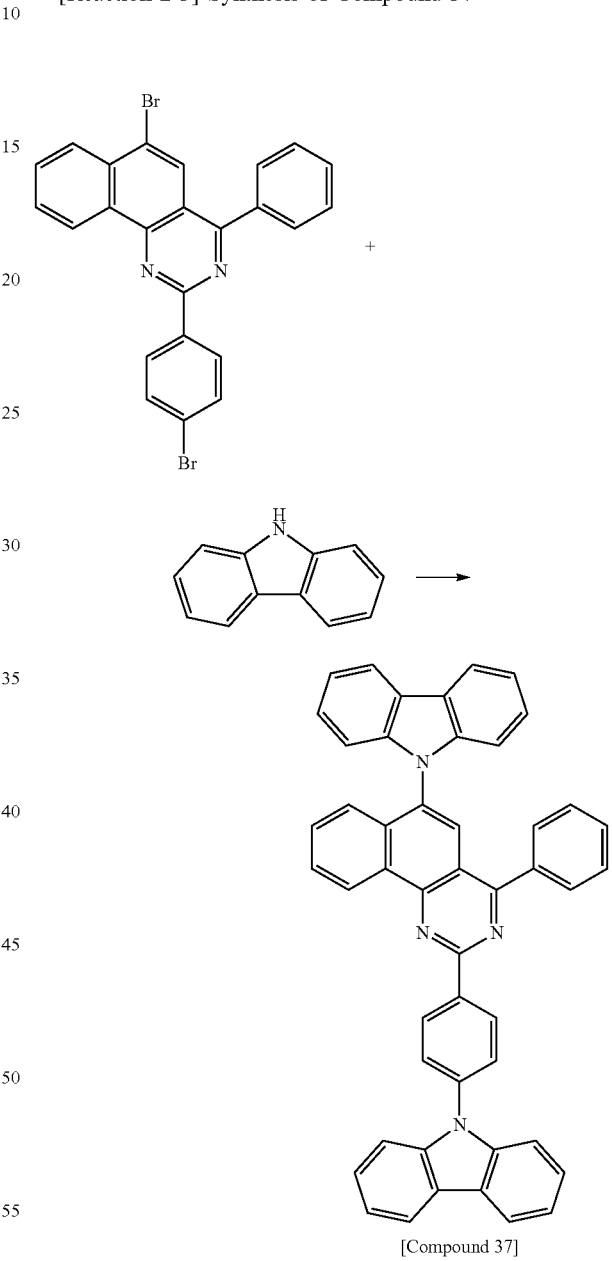

[Compound 37]

12.0 g (24 mmol) of Intermediate 2-b synthesized in Reaction 2-2, 9.8 g (59 mmol) of carbazole, 1.1 g (1.2 mmol) of tris(dibenzylideneacetone)dipalladium, 2.1 g (7.3 mmol) of tri-tert-butylphosphonium tetrafluoroborate, 11.8 g (122 mmol) of sodium tert-butoxide, and 60 mL of xylene were mixed and refluxed for 12 h. The reaction mixture was filtered at a high temperature and purified by column chromatography, affording 3.0 g of Compound 37 (yield 38%).

MS: m/z 663

Synthesis Example 3

Synthesis of Compound 19

[Reaction 3-1] Synthesis of Intermediate 3-a

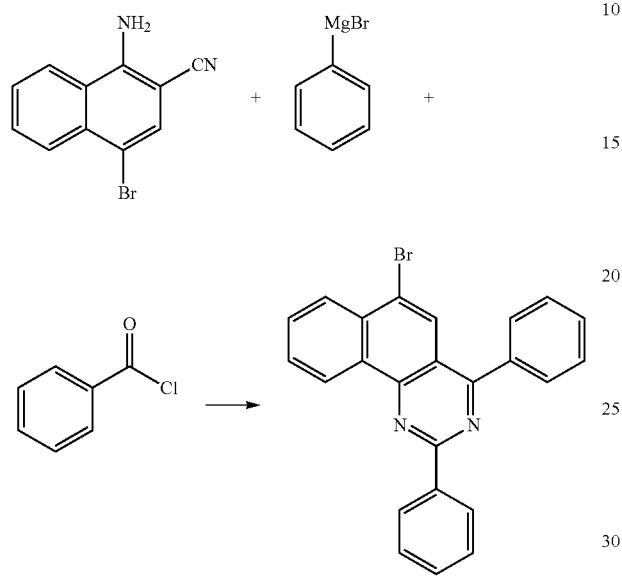

[Intermediate 3-a]

lp;1p12.5 g of Intermediate 3-a (yield 63%) was synthesized in the same manner as in Reaction 2-2, except that benzoyl chloride was used instead of 4-bromobenzoyl chloride.

[Reaction 3-2] Synthesis of Compound 19

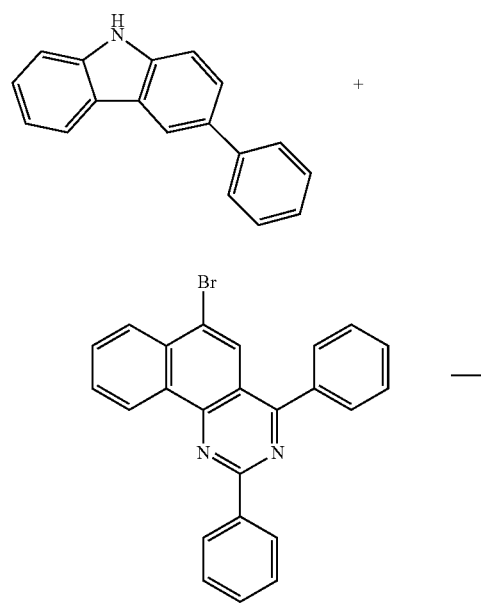

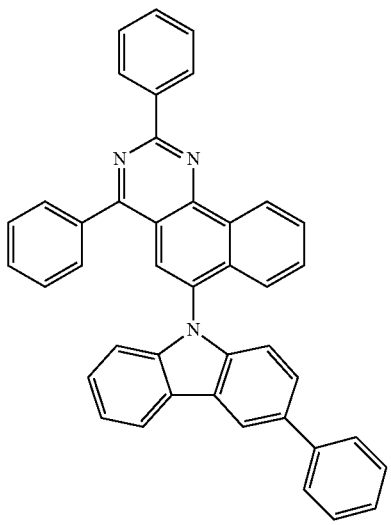

[Compound 19]

2.3 g of Compound 19 (yield 38%) was synthesized in the same manner as in Reaction 2-3, except that Intermediate 3-a synthesized in Reaction 3-1 and 3-phenylcarbazole were used instead of Intermediate 2-b and carbazole, respectively.

MS: m/z 574

Synthesis Example 4

Synthesis of Compound 20

[Reaction 4-1] Synthesis of Intermediate 4-a

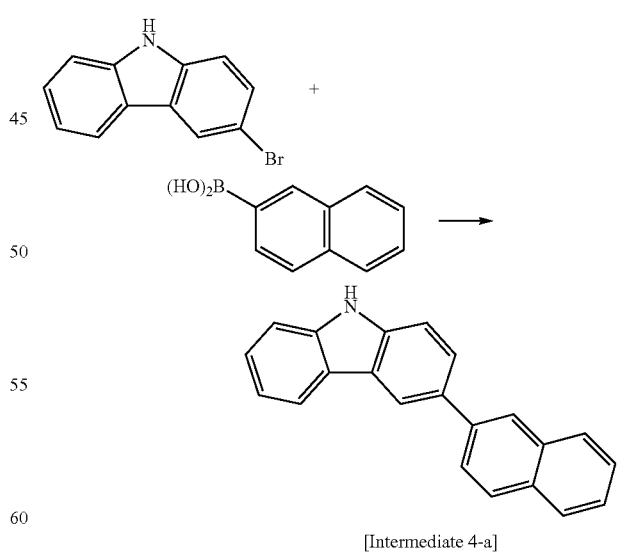

[Intermediate 4-a]

82.0 g of Intermediate 4-a (yield 63%) was synthesized in the same manner as in Reaction 1-6, except that 3-bromocarbazole and 2-naphthylboronic acid were used instead of Intermediate 1-d and Intermediate 1-e, respectively.

41

[Reaction 4-2] Synthesis of Compound 20

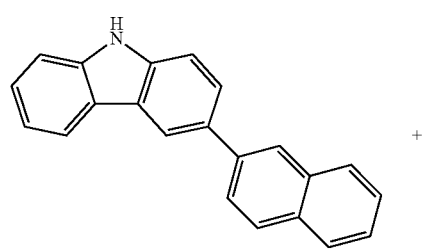

+

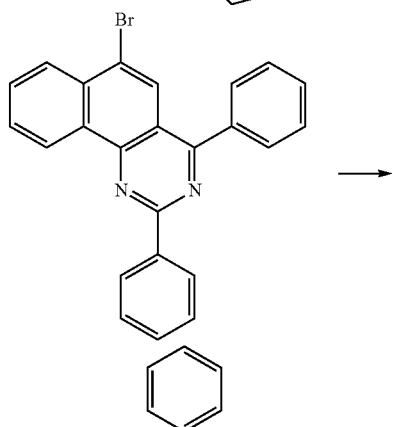

[Compound 20]

3.0 g of Compound 20 (yield 32%) was synthesized in the same manner as in Reaction 2-3, except that Intermediate 3-a synthesized in Reaction 3-1 and Intermediate 4-a synthesized in Reaction 4-1 were used instead of Intermediate 2-b and carbazole, respectively.

MS: m/z 624

Synthesis Example 5

Synthesis of Compound 21

[Reaction 5-1] Synthesis of Intermediate 5-a

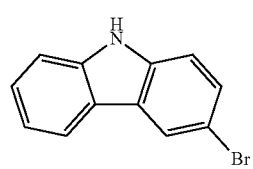

+

42

-continued

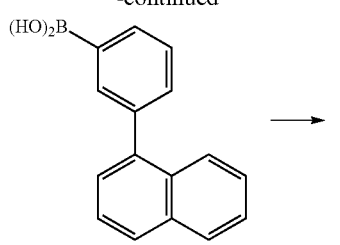

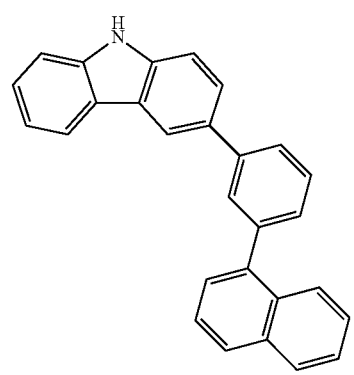

[Intermediate 5-a]

47.5 g of Intermediate 5-a (yield 68%) was synthesized in the same manner as in Reaction 1-6, except that 3-bromo-carbazole and 3-(1-naphthyl)phenylboronic acid were used instead of Intermediate 1-d and Intermediate 1-e, respectively.

[Reaction 5-2] Synthesis of Compound 21

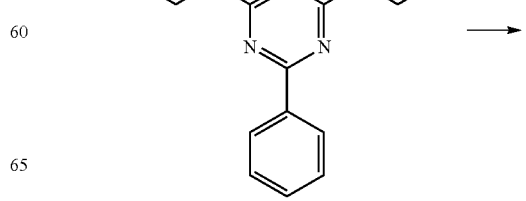

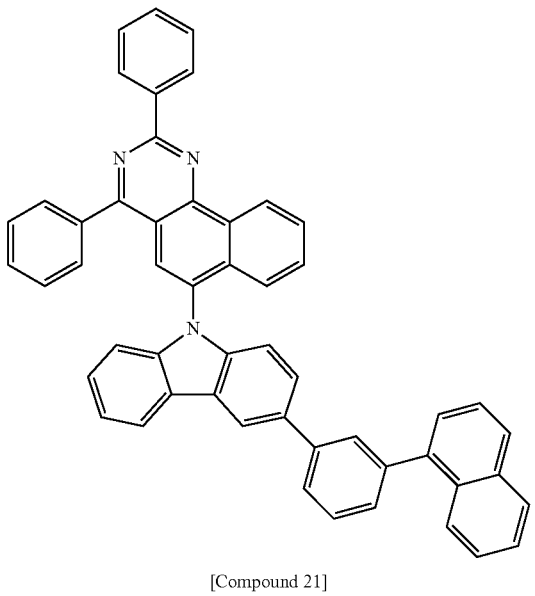

[Compound 21]

2.4 g of Compound 21 (yield 28%) was synthesized in the same manner as in Reaction 2-3, except that Intermediate 3-a synthesized in Reaction 3-1 and Intermediate 5-a synthesized in Reaction 5-1 were used instead of Intermediate 2-b and carbazole, respectively.

MS: m/z 700

Synthesis Example 6

Synthesis of Compound 48

[Reaction 6-1] Synthesis of Intermediate 6-a

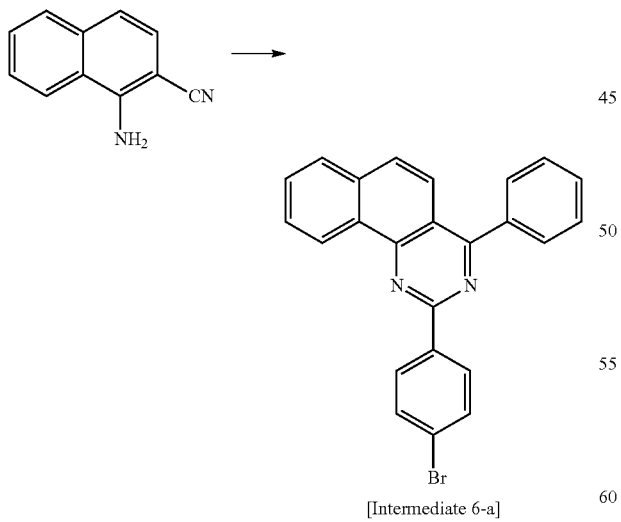

[Intermediate 6-a]

100 ml (100 mmol) of a 1 M solution of phenylmagnesium bromide in tetrahydrofuran and 100 mL of tetrahydrofuran were mixed and heated to 45° C. A solution of 5.91 g (50 mmol) of Intermediate 1-a synthesized in Reaction 1-1 in 50 mL of tetrahydrofuran was added dropwise. The mixture was refluxed for 2 h. After cooling to 0° C., a solution of 13.2 g (60 ml) of 4-bromobenzoyl chloride in 100 ml of tetrahydrofuran was added dropwise. The resulting mixture was heated to 45° C., stirred for 2 h, cooled to 0° C., and added with a saturated aqueous solution of ammonium chloride to precipitate a solid. The solid was collected by filtration and recrystallized from toluene, affording 10.8 g of Intermediate 6-a (yield 60%).

[Reaction 6-2] Synthesis of Compound 48

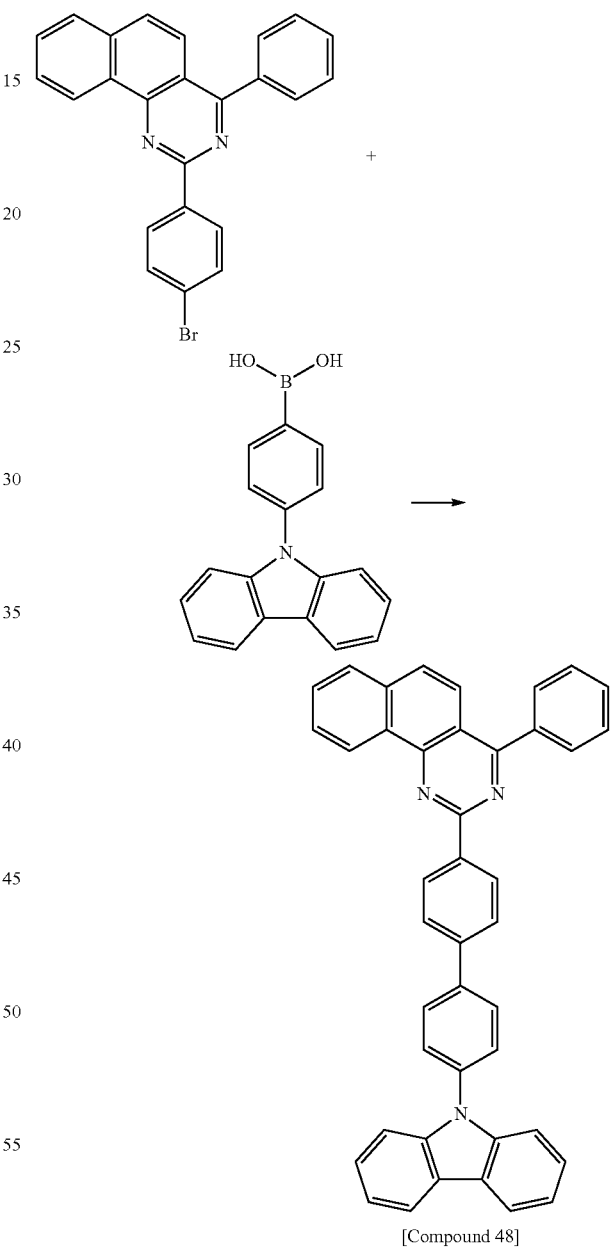

[Compound 48]

3.9 g of Compound 48 (yield 44%) was synthesized in the same manner as in Reaction 1-6, except that Intermediate 6-a synthesized in Reaction 6-1 and 4-(9H-carbazol-9-yl)phenylboronic acid were used instead of Intermediate 1-d and Intermediate 1-e, respectively.

MS: m/z 574

Synthesis Example 7

Synthesis of Compound 50

[Reaction 7-1] Synthesis of Intermediate 7-a

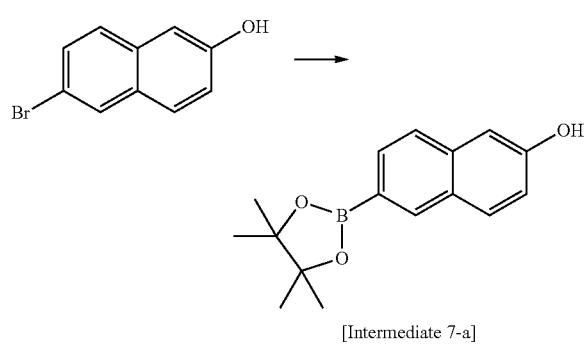

[Intermediate 7-a]

6-Bromo-2-naphthol (50 g, 224 mmol), bis(pinacolato)diboron (85.4 g, 336 mmol), [1,1'-bis(diphenylphosphino)ferrocene]palladium (II) chloride (4.9 g, 7 mmol), potassium acetate (66 g, 672 mmol), and 500 ml of toluene were mixed and refluxed for 12 h. The reaction mixture was filtered at a high temperature and purified by column chromatography, affording 43 g of Intermediate 7-a (yield 71%).

[Reaction 7-2] Synthesis of Intermediate 7-b

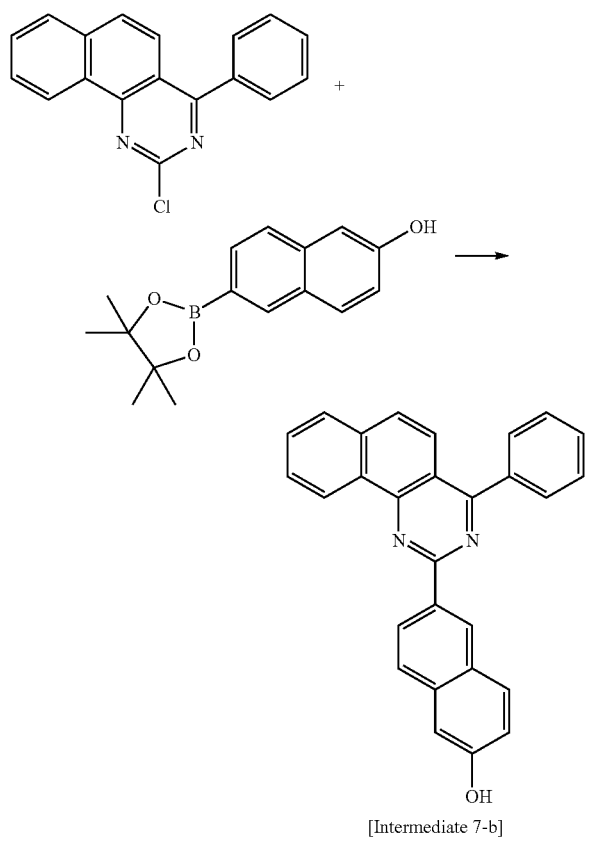

[Intermediate 7-b]

24.5 g of Intermediate 7-b (yield 99%) was synthesized in the same manner as in Reaction 1-6, except that Intermediate 1-c synthesized in Reaction 1-3 and Intermediate 7-a synthesized in Reaction 7-1 were used instead of Intermediate 1-d and Intermediate 1-e, respectively.

[Reaction 7-3] Synthesis of Intermediate 7-c

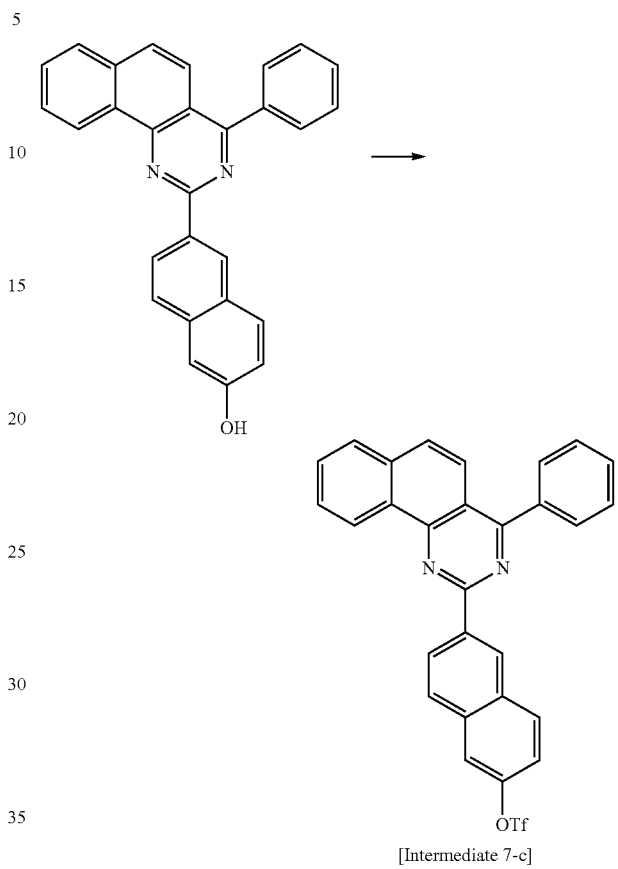

[Intermediate 7-c]

Intermediate 7-b (39 g, 98 mmol) synthesized in Reaction 7-2, 10.1 g (127 mmol) of pyridine, and 390 ml of methylene chloride were mixed and cooled to 0° C. To the mixture was added dropwise 35.9 g (127 mmol) of trifluoromethanesulfonic anhydride. The resulting mixture was allowed to warm to room temperature, followed by stirring for 2 h. After cooling to 0° C., water was added to precipitate a solid. The solid was collected by filtration and recrystallized, affording 38.1 g of Intermediate 7-c (yield 73.4%).

[Reaction 7-4] Synthesis of Compound 50

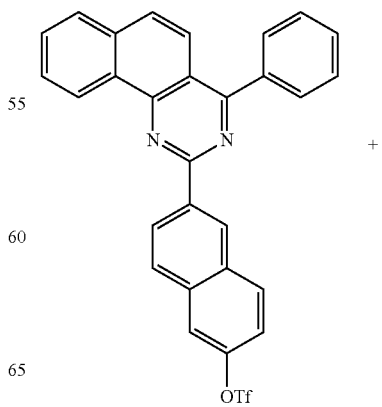

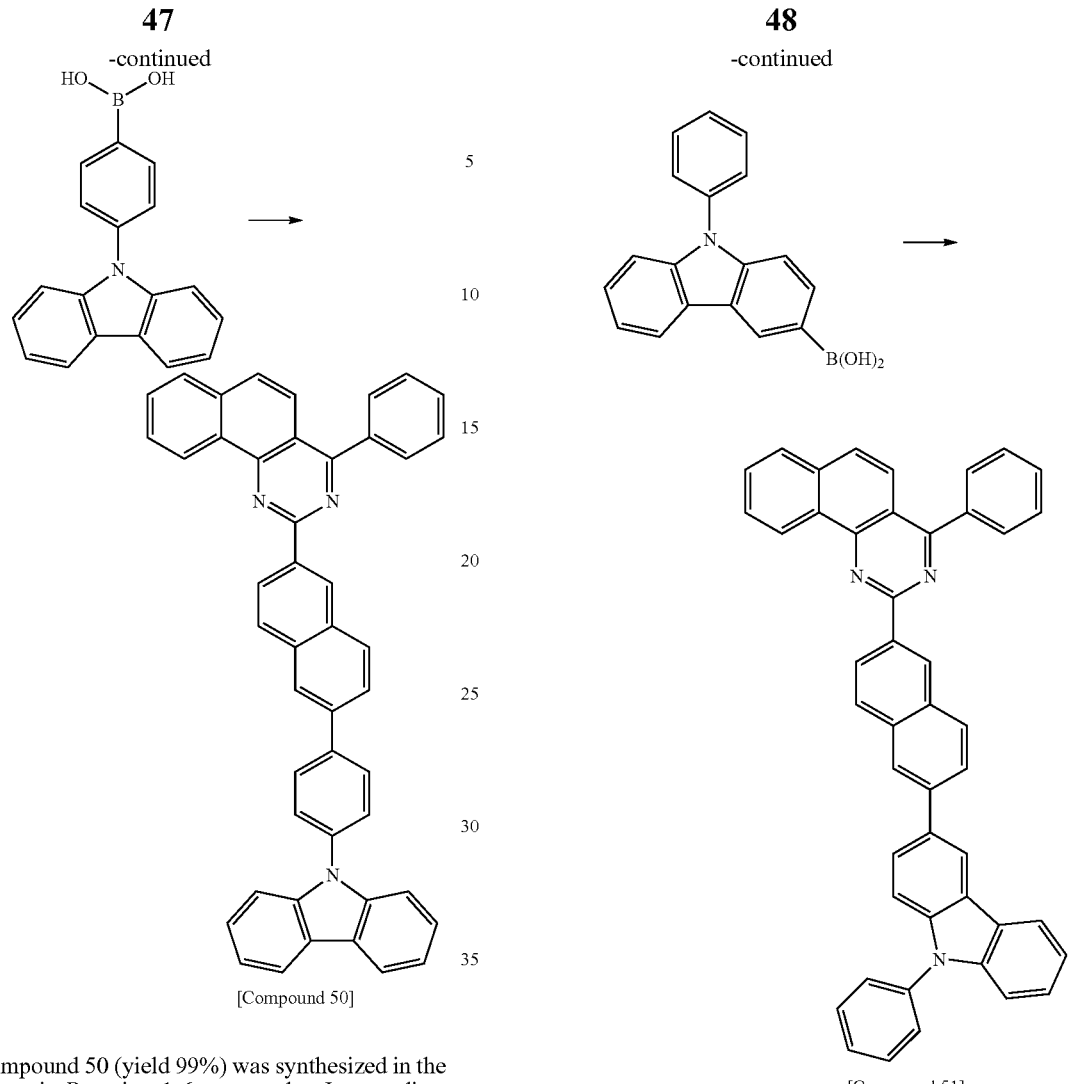

[Compound 50]

5.5 g of Compound 50 (yield 99%) was synthesized in the same manner as in Reaction 1-6, except that Intermediate 7-c synthesized in Reaction 7-3 and 4-(9H-carbazol-9-yl)phenylboronic acid were used instead of Intermediate 1-d and Intermediate 1-e, respectively.

MS: m/z 624

Synthesis Example 8

Synthesis of Compound 51

[Reaction 8-1] Synthesis of Compound 51

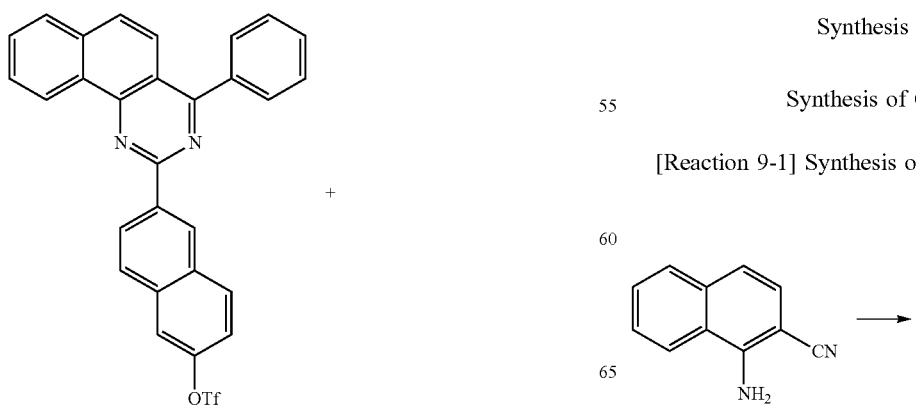

[Compound 51]

3.9 g of Compound 51 (yield 46%) was synthesized in the same manner as in Reaction 1-6, except that Intermediate 7-c synthesized in Reaction 7-3 and 9-phenyl-9H-carbazole-3-boronic acid were used instead of Intermediate 1-d and Intermediate 1-e, respectively.

MS: m/z 624

Synthesis Example 9

Synthesis of Compound 49

[Reaction 9-1] Synthesis of Intermediate 9-a

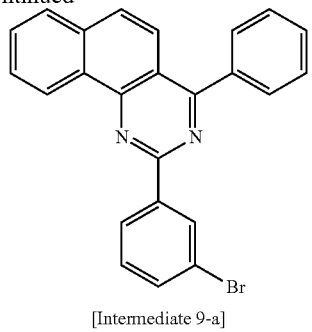

[Intermediate 9-a]

12.3 g of Intermediate 9-1 (yield 62%) was synthesized in the same manner as in Reaction 6-1, except that 3-bromobenzoyl chloride was used instead of 4-bromobenzoyl chloride.

[Reaction 9-2] Synthesis of Compound 49

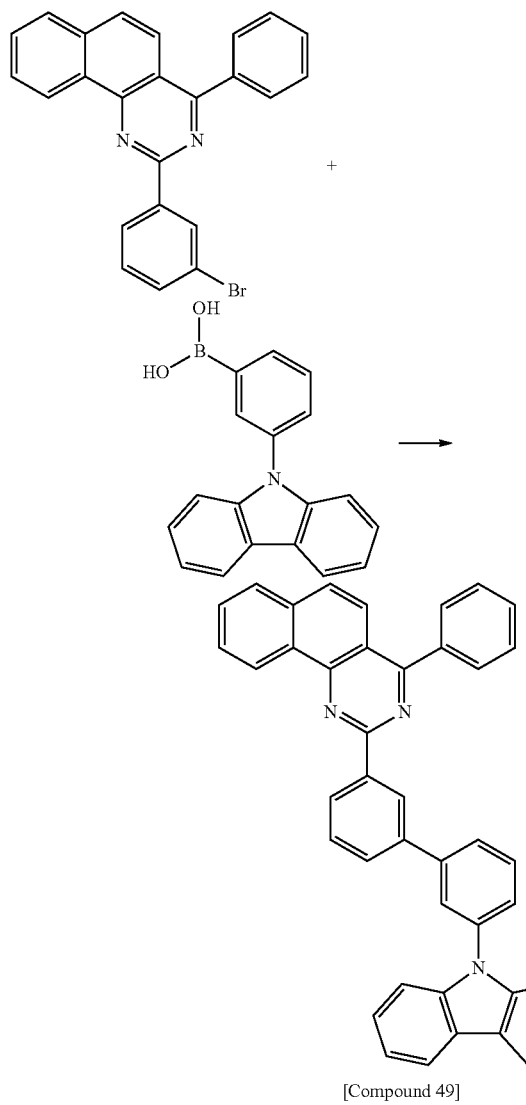

[Compound 49]

8.5 g of Intermediate 6-b (yield 87%) was synthesized in the same manner as in Reaction 1-6, except that Intermediate 9-a synthesized in Reaction 9-1 and 3-(9H-carbazol-9-yl)phenylboronic acid were used instead of Intermediate 1-d and Intermediate 1-e, respectively.

MS: m/z 574

Synthesis Example 10

Synthesis of Compound 42

[Reaction 10-1] Synthesis of Compound 42

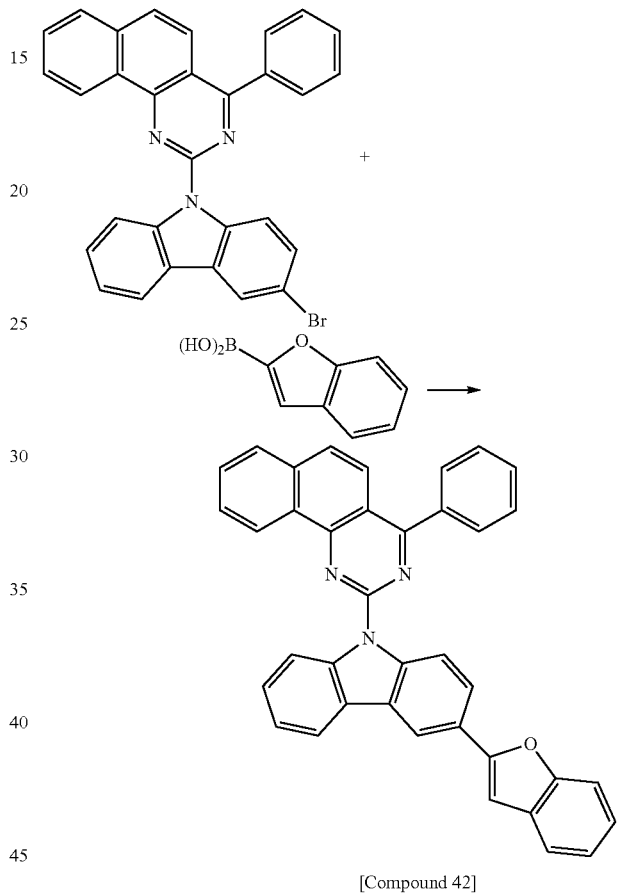

[Compound 42]

6.3 g of Intermediate 6-b (yield 72%) was synthesized in the same manner as in Reaction 1-6, except that benzofuran-2-boronic acid was used instead of Intermediate 1-e.

MS: m/z 538

Synthesis Example 11

Synthesis of Compound 59

[Reaction 11-1] Synthesis of Intermediate 11-a

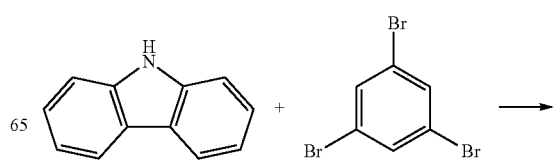

[Reaction 11-3] Synthesis of Compound 59

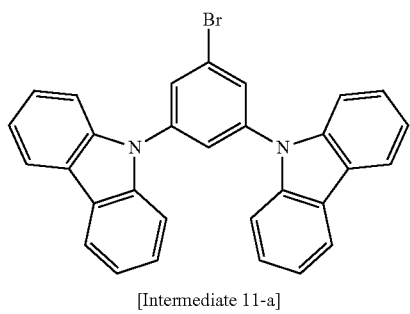

[Intermediate 11-a]

Carbazole (40.0 g, 239 mmol), 1,3,5-tribromobenzene (113.0 g, 359 mmol), copper iodide (2.3 g, 12 mmol), potassium phosphate (101.6 g, 479 mmol), 1,2-cyclohexanediamine (54.6 g, 479 mmol), and 400 mL of toluene were mixed and refluxed for 12 h. The reaction mixture was filtered at a high temperature and purified by column chromatography, affording 15.0 g of Intermediate 11-a (yield 15%).

[Reaction 11-2] Synthesis of Intermediate 11-b

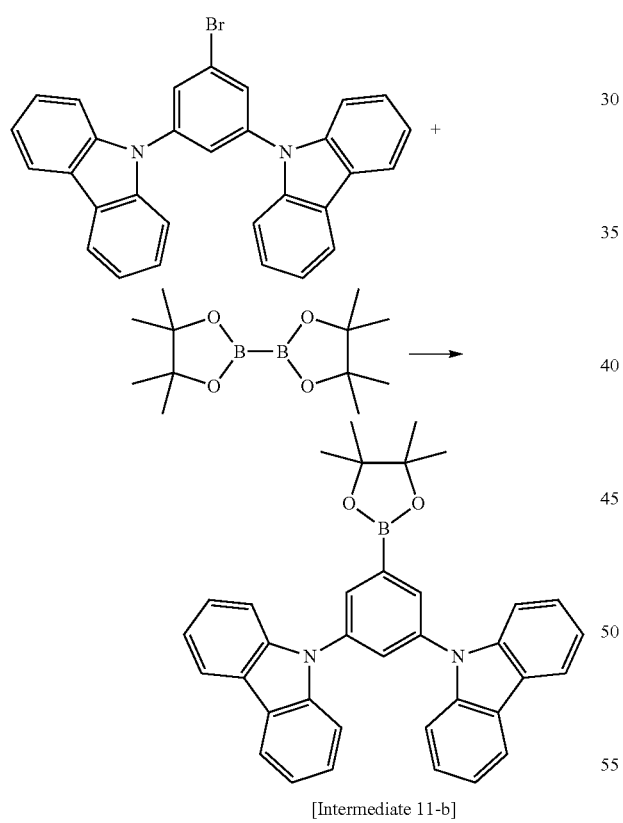

[Intermediate 11-b]

Intermediate 11-a (19.0 g, 39 mmol) synthesized in Reaction 11-1, bis(pinacolato)diboron (13.0 g, 51 mmol), [1,1'-bis(diphenylphosphino)ferrocene]palladium (II) chloride (0.9 g, 1 mmol), potassium acetate (11.5 g, 117 mmol), and 150 mL of toluene were mixed and refluxed for 12 h. The reaction mixture was filtered at a high temperature and purified by column chromatography, affording 14.8 g of Intermediate 11-b (yield 71%).

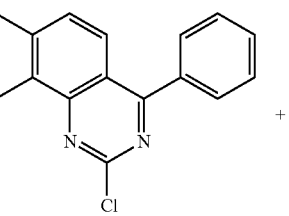

+

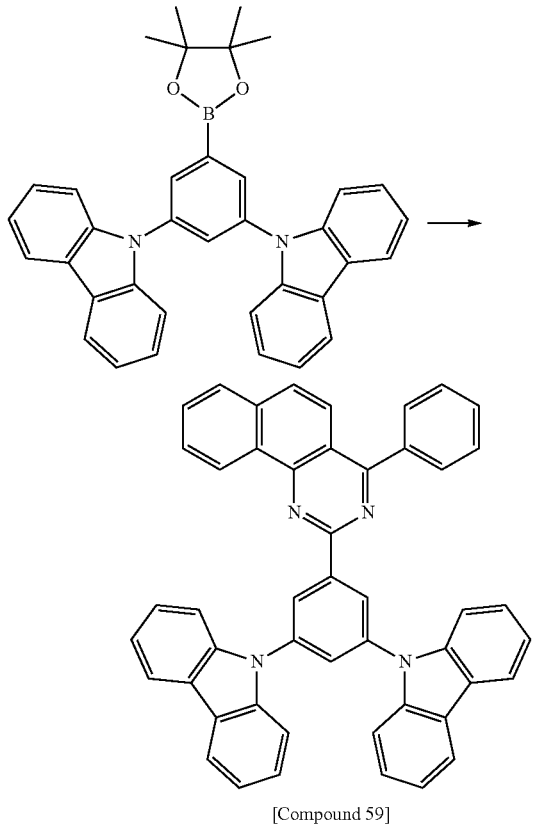

[Compound 59]

4.0 g of Compound 59 (yield 40%) was synthesized in the same manner as in Reaction 1-6, except that Intermediate 1-c synthesized in Reaction 1-3 and Intermediate 11-b synthesized in Reaction 11-2 were used instead of Intermediate 1-d and Intermediate 1-e, respectively.

MS: m/z 663

Synthesis Example 12

Synthesis of Compound 60

[Reaction 12-1] Synthesis of Intermediate 12-a

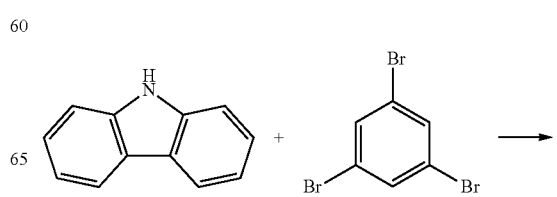

-continued

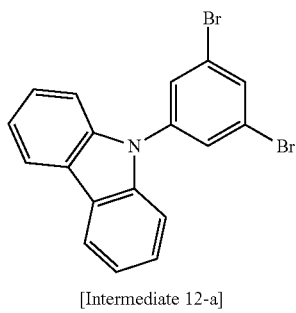

[Intermediate 12-a]

Carbazole (40.0 g, 239 mmol), 1,3,5-tribromobenzene (113.0 g, 359 mmol), copper iodide (2.3 g, 12 mmol), potassium phosphate (101.6 g, 479 mmol), 1,2-cyclohexanediamine (54.6 g, 479 mmol), and 400 mL of toluene were mixed and refluxed for 12 h. The reaction mixture was filtered at a high temperature and purified by column chromatography, affording 34.0 g of Intermediate 12-a (yield 35%).

[Reaction 12-2] Synthesis of Intermediate 12-b

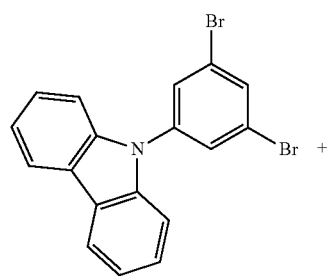

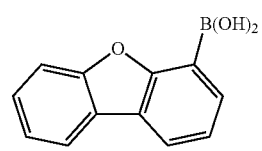

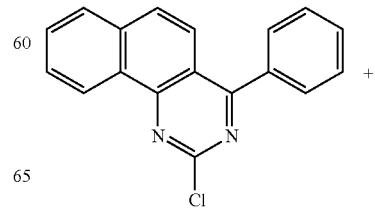

[Intermediate 12-b]

19.0 g of Intermediate 12-b (yield 78%) was synthesized in the same manner as in Reaction 1-6, except that Intermediate 12-a synthesized in Reaction 12-1 and dibenzo- furan-4-boronic acid were used instead of Intermediate 1-d and Intermediate 1-e, respectively.

[Reaction 12-3] Synthesis of Intermediate 12-c

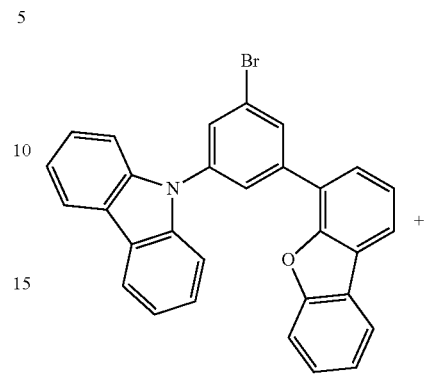

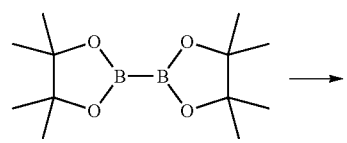

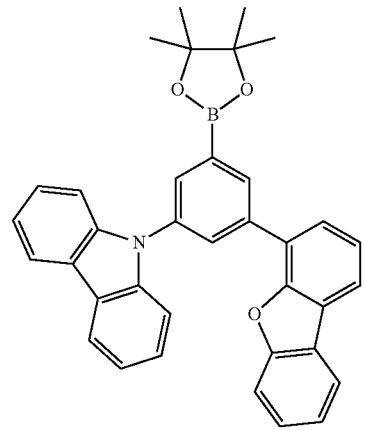

[Intermediate 12-c]

13.4 g of Intermediate 12-c (yield 64%) was synthesized in the same manner as in Reaction 11-2, except that Intermediate 12-b synthesized in Reaction 12-2 was used instead of Intermediate 11-a.

[Reaction 12-4] Synthesis of Compound 60

-continued

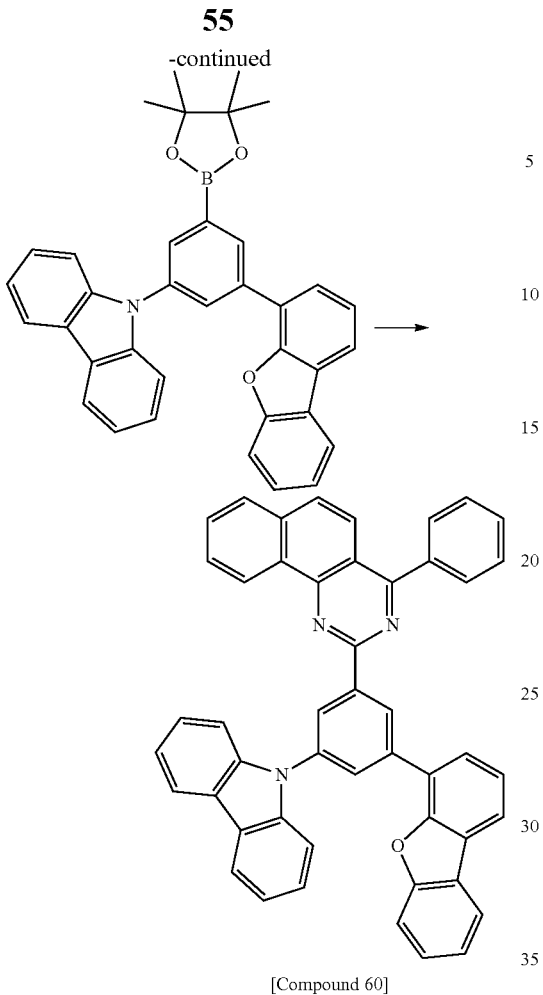
[Compound 60]

4.7 g of Compound 60 (yield 45%) was synthesized in the same manner as in Reaction 1-6, except that Intermediate 1-c synthesized in Reaction 1-3 and Intermediate 12-c synthesized in Reaction 12-3 were used instead of Intermediate 1-d and Intermediate 1-e, respectively.

MS: m/z 664

Synthesis Example 13

Synthesis of Compound 43

[Reaction 13-1] Synthesis of Intermediate 13-a

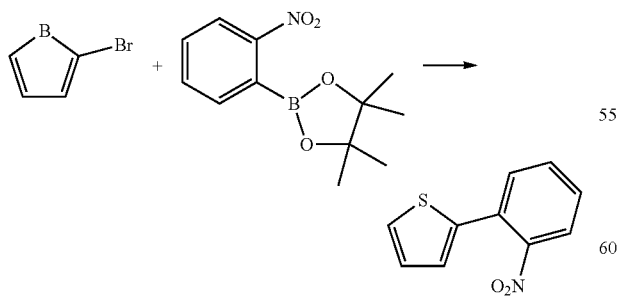

20.0 g of Intermediate 13-a (yield 35%) was synthesized in the same manner as in Reaction 1-6, except that 2-bromothiophene (45.0 g, 2 76 mmol) and 2-nitrophenylboronic acid pinacol ester (89.3 g, 359 mmol) were used instead of Intermediate 1-d and Intermediate 1-e, respectively.

[Reaction 13-2] Synthesis of Intermediate 13-b

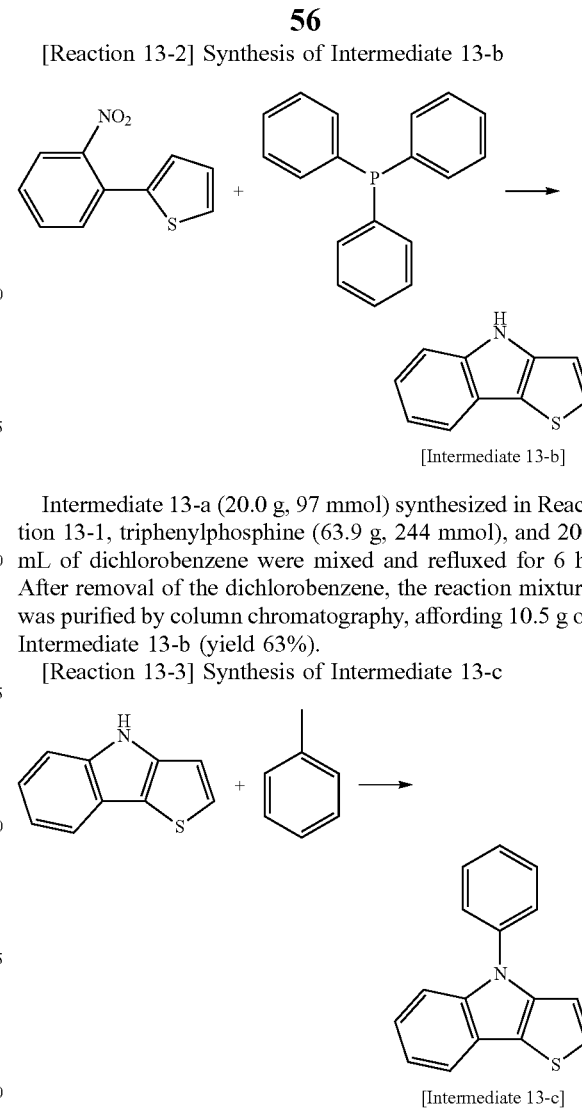
[Intermediate 13-b]

Intermediate 13-a (20.0 g, 97 mmol) synthesized in Reaction 13-1, triphenylphosphine (63.9 g, 244 mmol), and 200 mL of dichlorobenzene were mixed and refluxed for 6 h. After removal of the dichlorobenzene, the reaction mixture was purified by column chromatography, affording 10.5 g of Intermediate 13-b (yield 63%).

[Reaction 13-3] Synthesis of Intermediate 13-c

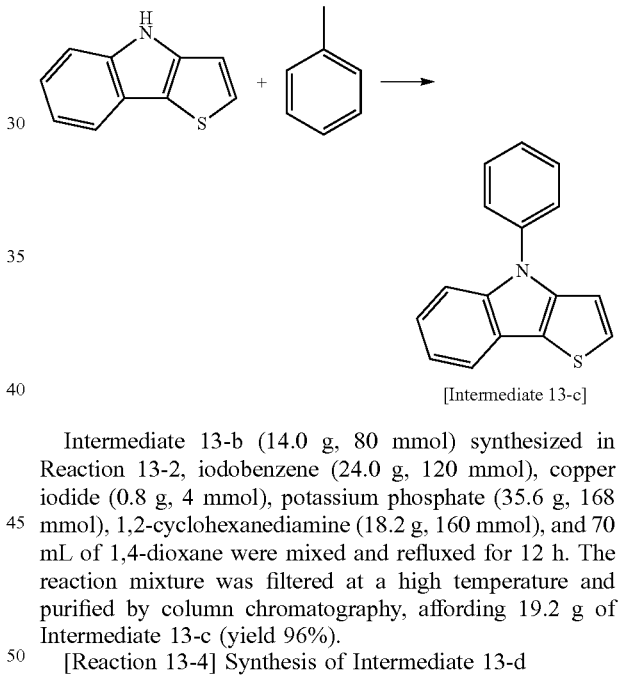
[Intermediate 13-c]

Intermediate 13-b (14.0 g, 80 mmol) synthesized in Reaction 13-2, iodobenzene (24.0 g, 120 mmol), copper iodide (0.8 g, 4 mmol), potassium phosphate (35.6 g, 168 mmol), 1,2-cyclohexanediamine (18.2 g, 160 mmol), and 70 mL of 1,4-dioxane were mixed and refluxed for 12 h. The reaction mixture was filtered at a high temperature and purified by column chromatography, affording 19.2 g of Intermediate 13-c (yield 96%).

[Reaction 13-4] Synthesis of Intermediate 13-d

Intermediate 13-c (12.0 g, 39 mmol) synthesized in Reaction 13-c and 120 mL of tetrahydrofuran were mixed and cooled to −78° C. After dropwise addition of n-butyllithium (36.10 g, 58 mmol), the mixture was allowed to warm to room temperature, followed by stirring for 12 h. The mixture was cooled to −78° C. and iodine (14.7 g, 58 mmol) was added thereto. The resulting mixture was allowed to warm to room temperature, followed by stirring for 12 h. The reaction mixture was added with an aqueous solution of sodium thiosulfate, extracted with ethyl acetate, and recrystallized from heptane, affording 7.2 g of Intermediate 13-d (yield 54%).

[Reaction 13-5] Synthesis of Intermediate 13-e

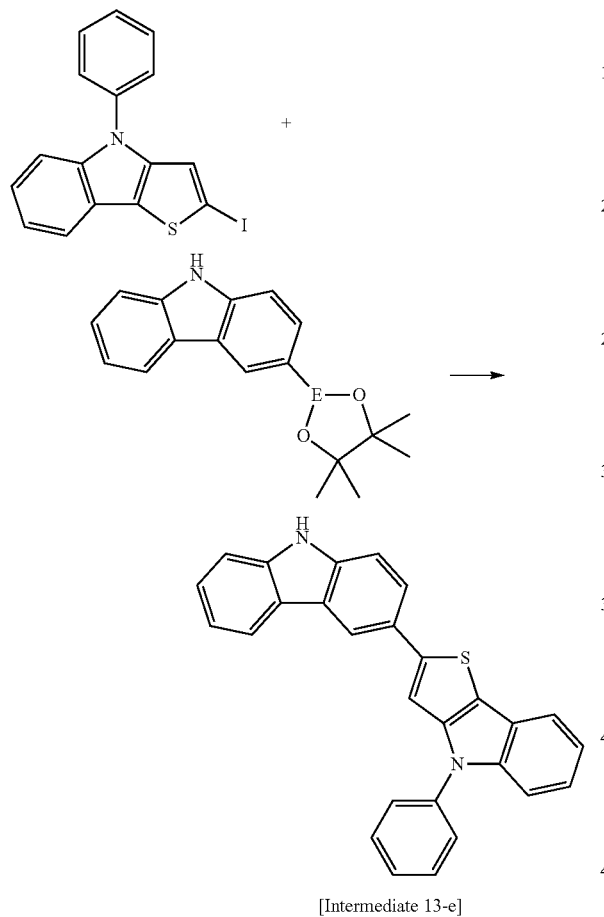

[Intermediate 13-e]

6.5 g of Intermediate 13-e (yield 40%) was synthesized in the same manner as in Reaction 1-6, except that Intermediate 13-d (14.7 g, 39 mmol) synthesized in Reaction 13-4 and 3-(4,4,5,5-tetramethyl-[1,3,2]dioxaborolan-2-yl)-9H-carbazole (89.3 g, 359 mmol) were used instead of Intermediate 1-d and Intermediate 1-e, respectively.

[Reaction 13-6] Synthesis of Compound 43

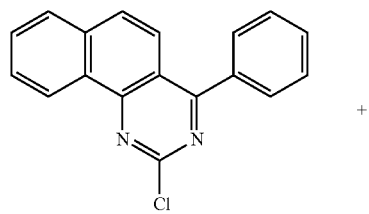

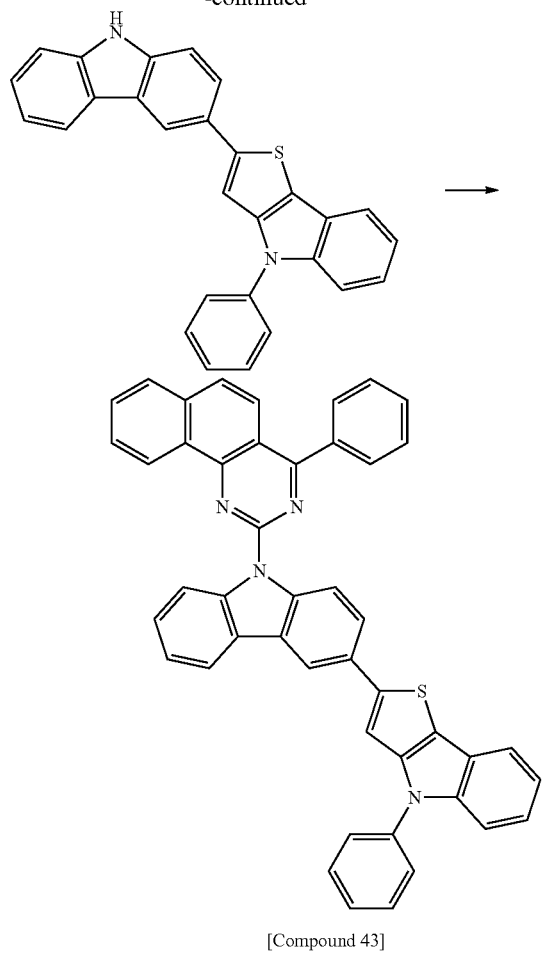

[Compound 43]

3.5 g of Compound 43 (yield 30%) was synthesized in the same manner as in Reaction 1-4, except that Intermediate 13-e (14.7 g, 39 mmol) synthesized in Reaction 13-5 was used instead of 3-bromo-9H-carbazole.

MS: m/z 669

Synthesis Example 14

Synthesis of Compound 44

[Reaction 14-1] Synthesis of Compound 44

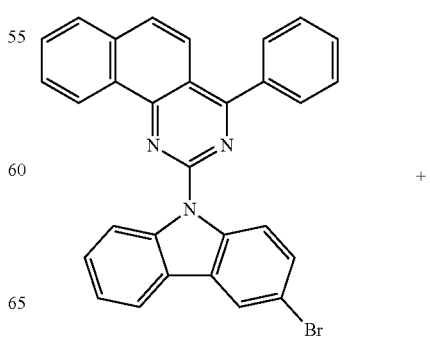

-continued

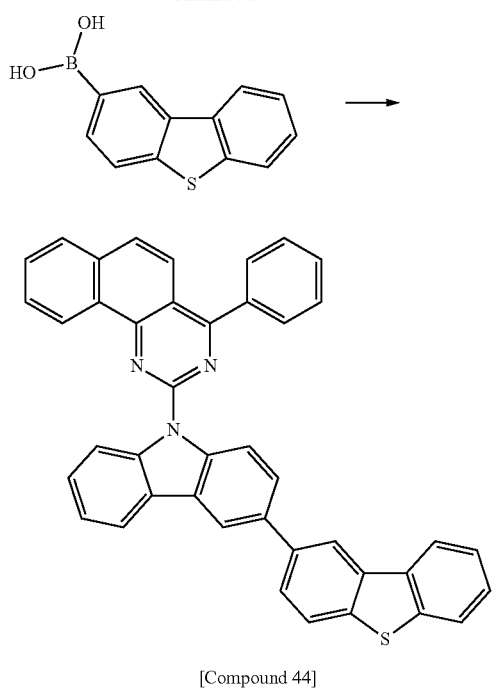

[Compound 44]

7.2 g of Compound 44 (yield 80%) was synthesized in the same manner as in Reaction 1-6, except that dibenzothiophene-2-boronic acid was used instead of Intermediate 1-e.

MS: m/z 604

Synthesis Example 15

Synthesis of Compound 15

[Reaction 15-1] Synthesis of Compound 15

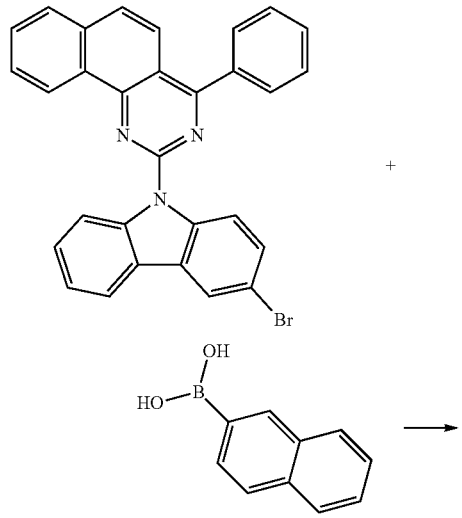

-continued

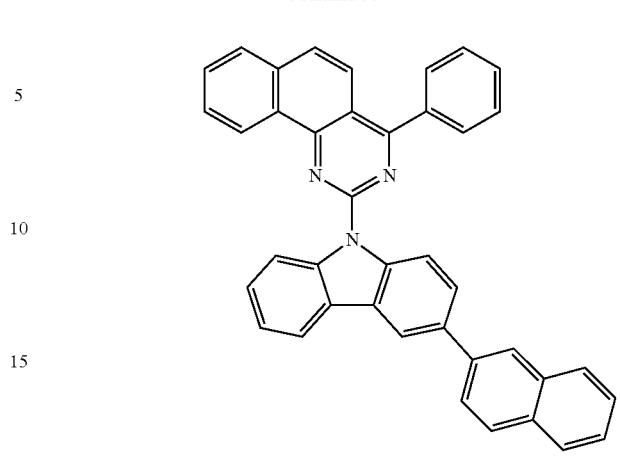

[Compound 15]

8.1 g of Compound 44 (yield 74%) was synthesized in the same manner as in Reaction 1-6, except that 2-naphthylboronic acid was used instead of Intermediate 1-e.

MS: m/z 548

Synthesis Example 16

Synthesis of Compound 18

[Reaction 16-1] Synthesis of Compound 18

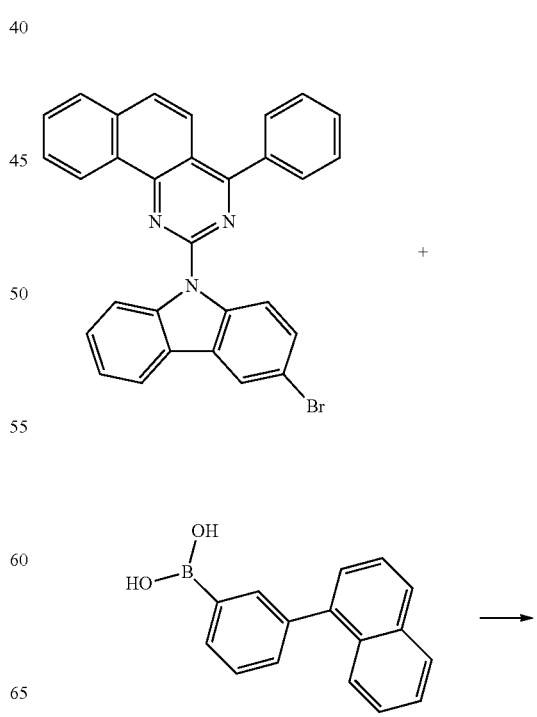

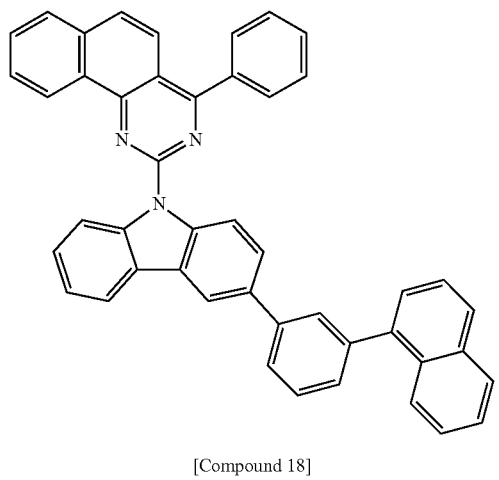

[Compound 18]

6.2 g of Compound 44 (yield 73%) was synthesized in the same manner as in Reaction 1-6, except that 3-(1-naphthyl)phenylboronic acid was used instead of Intermediate 1-e.

MS: m/z 624

Synthesis Example 17

Synthesis of Compound 32

[Reaction 17-1] Synthesis of Intermediate 17-a

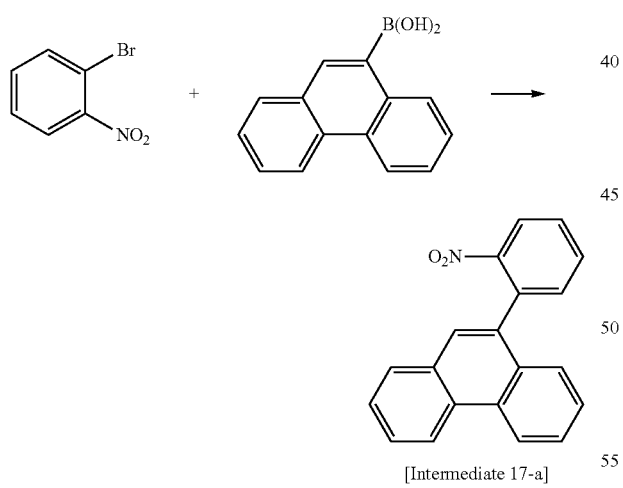

[Intermediate 17-a]

25.0 g (124 mmol) of 1-bromo-2-nitrobenzene, 33.0 g (149 mmol) of 9-phenanthrylboronic acid, 2.9 g (3 mmol) of tetrakis(triphenylphosphine)palladium, 34.2 g (248 mmol) of potassium carbonate, 250 mL of 1,4-dioxane, 250 mL of toluene, and 100 mL of distilled water were mixed and refluxed for 12 h. The reaction mixture was extracted with ethyl acetate and purified by column chromatography, affording 33.2 g of Intermediate 17-a (yield 90%).

[Reaction 17-2] Synthesis of Intermediate 17-b

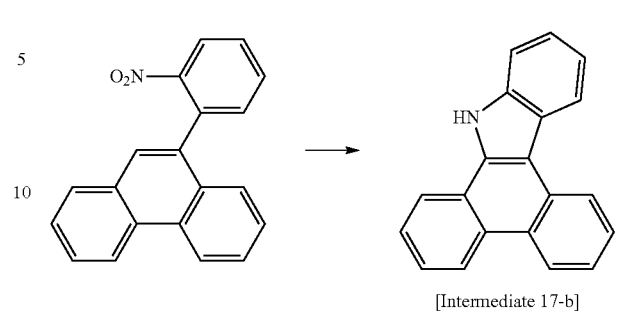

[Intermediate 17-b]

23.0 g of Intermediate 17-b (yield 77%) was synthesized in the same manner as in Reaction 13-2, except that Intermediate 17-a synthesized in Reaction 17-1 was used instead of Intermediate 13-a.

[Reaction 17-3] Synthesis of Compound 32

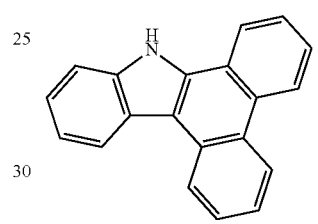

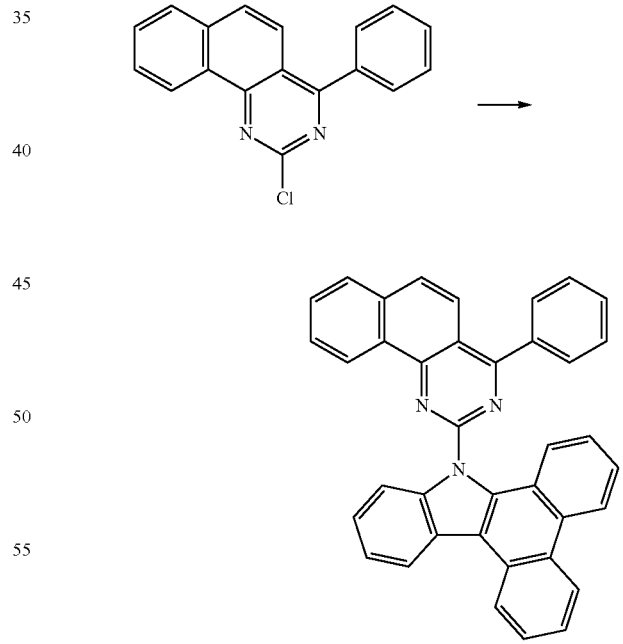

[Compound 32]

7.4 g of Compound 32 (yield 30%) was synthesized in the same manner as in Reaction 1-4, except that Intermediate 17-b synthesized in Reaction 17-2 was used instead of 3-bromo-9H-carbazole.

MS: m/z 522

Examples 1-7

Fabrication of Organic Light Emitting Diodes

ITO glass was patterned to have a light emitting area of 2 mm×2 mm, followed by cleaning. After the cleaned ITO glass was mounted in a vacuum chamber, the base pressure was adjusted to $1\times10^{-6}$ torr. DNTPD (700 Å), α-NPD (300 Å), Compound 15, 18, 19, 20, 29, 34 or 44+RD-1 (10%) (300 Å), and Compound A:Liq=1:1 (250 Å), Liq (10 Å), and Al (1,000 Å) were sequentially deposited on the ITO to form organic layers, completing the fabrication of an organic light emitting diode. The luminescent properties of the organic light emitting diode were measured at 0.4 mA.

The structures of the DNTPD, NPD, RD-1, Compound A, and Liq are as follows:

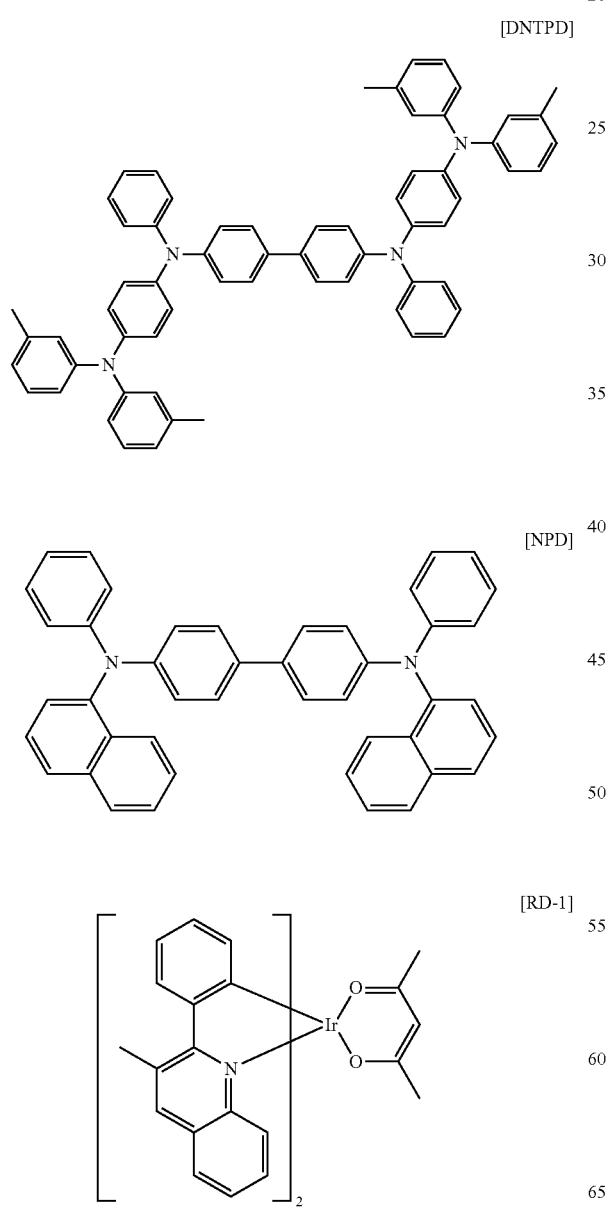

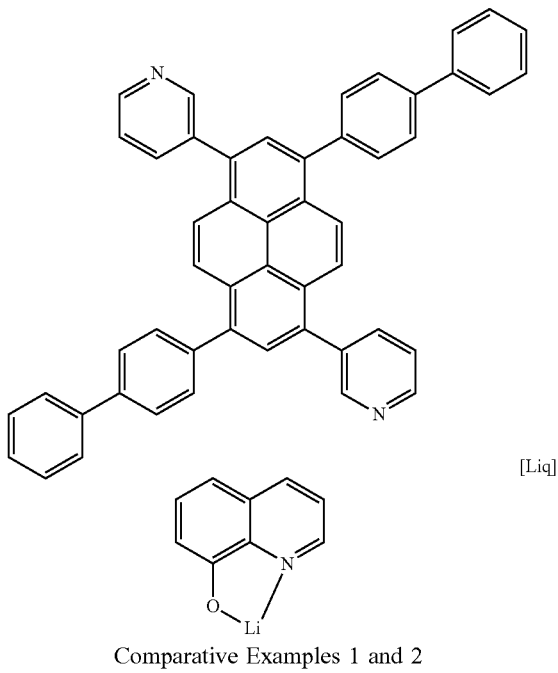

Comparative Examples 1 and 2

An organic light emitting diode was fabricated in the same manner as in Examples 1-7, except that BAlq (Comparative Example 1) or Compound B (Comparative Example 2) was used instead of the inventive organic compounds. BAlq and Compound B are phosphorescent host materials well known in the art and their structures are as follows:

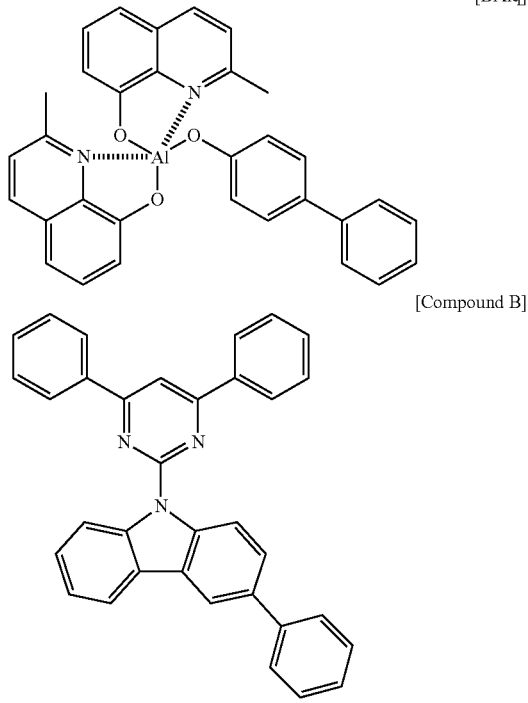

The organic electroluminescence devices fabricated in Examples 1-7 and Comparative Example 1-2 were measured for voltage, current density, luminance, color coordinates, and life. The results are shown in Table 1. $T_{95}$ indicates the time at which the luminance of each device was decreased to 95% of the initial luminance (3000 cd/m²).

TABLE 1

| Example No. | Host | Doping concentration (%) | Current density (V) | Luminance (Cd/m$^2$) | CIEx | CIEy | Life (T$_{95}$, hr) |
|---|---|---|---|---|---|---|---|
| Comparative Example 1 | BAlq | 10 | 6.2 | 1470 | 0.665 | 0.334 | 40 |
| Comparative Example 2 | B | 10 | 4.9 | 1210 | 0.664 | 0.335 | 10 |
| Example 1 | 15 | 10 | 4.5 | 1900 | 0.665 | 0.334 | 340 |
| Example 2 | 18 | 10 | 4.3 | 1910 | 0.665 | 0.334 | 300 |
| Example 3 | 19 | 10 | 3.5 | 1960 | 0.665 | 0.335 | 280 |
| Example 4 | 20 | 10 | 3.3 | 2000 | 0.666 | 0.333 | 260 |
| Example 5 | 29 | 10 | 4.0 | 1930 | 0.664 | 0.335 | 240 |
| Example 6 | 34 | 10 | 3.6 | 1750 | 0.664 | 0.335 | 270 |
| Example 7 | 44 | 10 | 4.3 | 2010 | 0.665 | 0.334 | 300 |

As can be seen from the results in Table 1, the inventive organic compounds had much lower driving voltages than BAlq, which is widely known as a phosphorescent host material, and had higher luminous efficiencies and longer lives than BAlq and Compound B.

INDUSTRIAL APPLICABILITY

The organic electroluminescence devices employing the organic light emitting compounds according to the present invention can be driven at low voltages compared to conventional devices employing phosphorescent host materials. The low-voltage driving leads to high power efficiency while at the same time achieving improved luminous efficiency and life characteristics. Therefore, the organic electroluminescence devices of the present invention are suitable for use in systems selected from flat panel displays, flexible displays, monochromatic flat panel lighting systems, white flat panel lighting systems, flexible monochromatic lighting systems, and flexible white lighting systems.

The invention claimed is:

1. An organic light emitting compound represented by Formula 1:

[Formula 1]

wherein A is selected from:

-continued wherein $X_1$ to $X_8$ are identical to or different from each other and are each independently N or $CR_o$, provided that when $CR_o$ exists in plurality, the $CR_o$ groups are identical to or different from each other;

$Z_1$ to $Z_4$ are each independently N or are $CR_1$ to $CR_4$, respectively;

L represents a linker and is a single bond or is selected from the following structures:

[Structure B1]

[Structure B2]

[Structure B3]

[Structure B4]

[Structure B5]

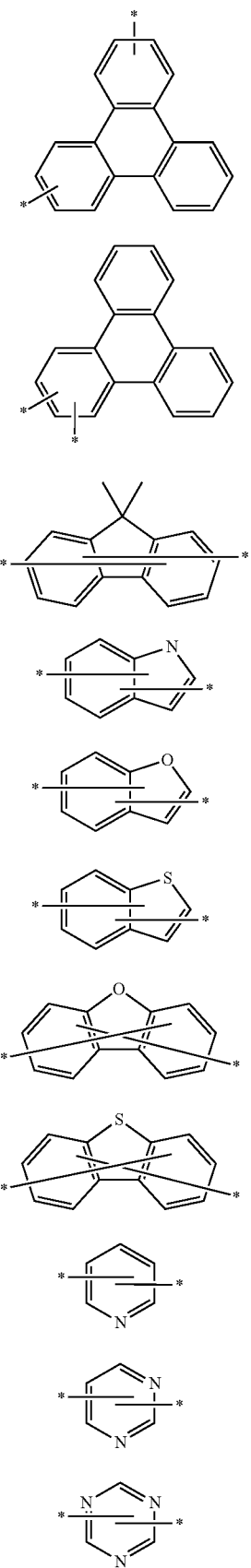

wherein hydrogen or deuterium atoms are optionally bonded to the carbon atoms of the aromatic rings and any one of $CR_o$ and $CR_1$ to $CR_8$ optionally replaces the nitrogen atoms;

n is an integer from 1 to 3, provided that when n is equal to or greater than 2, the plurality of L groups are identical to or different from each other;

$R_o$ and $R_1$ to $R_8$ are identical to or different from each other and are each independently selected from a hydrogen atom, a deuterium atom, substituted or unsubstituted $C_1$-$C_{30}$ alkyl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted $C_3$-$C_{60}$ cycloalkyl groups, substituted or unsubstituted $C_5$-$C_{30}$ cycloalkenyl groups, substituted or unsubstituted $C_5$-$C_{60}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_5$-$C_{60}$ arylthio groups, —$SiR_{11}R_{12}R_{13}$, and —$NR_{14}R_{15}$, $R_{11}$ to $R_{15}$ are identical to or different from each other and are each independently selected from a hydrogen atom, a deuterium atom, substituted or unsubstituted $C_1$-$C_{30}$ alkyl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted $C_3$-$C_{60}$ cycloalkyl groups, substituted or unsubstituted $C_5$-$C_{30}$ cycloalkenyl groups, substituted or unsubstituted $C_5$-$C_{60}$ aryloxy groups, substituted or unsubstituted $C_1$-$C_{30}$ alkylthioxy groups, substituted or unsubstituted $C_5$-$C_{30}$ arylthioxy groups, and substituted or unsubstituted $C_5$-$C_{60}$ arylthio groups, and m is an integer from 1 to 3;

wherein each

is selected from:

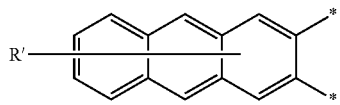

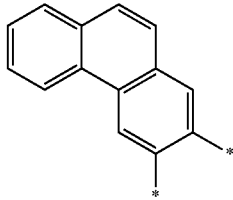

C7

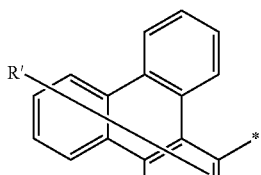

C9

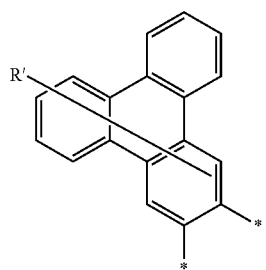

C10

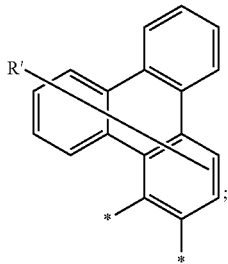

C11 and wherein each asterisk (*) represents a bonding site and each R' has the same meaning as $R_1$ to $R_8$.

2. The organic light emitting compound according to claim 1, wherein the compound of Formula 1 is selected from compounds represented by Formulae 2 to 8:

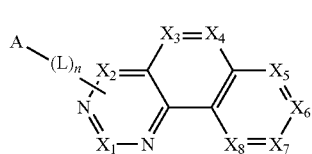

[Formula 2]

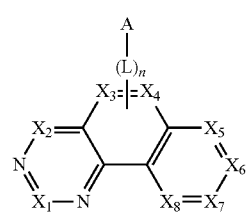

[Formula 3]

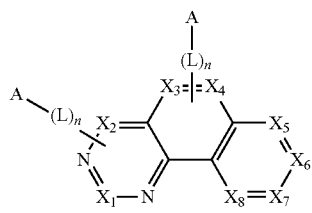

[Formula 4]

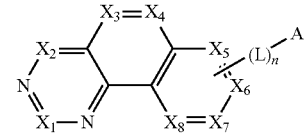

[Formula 5]

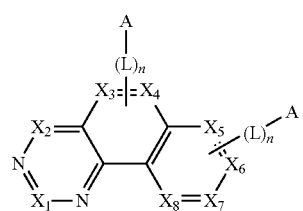

[Formula 6]

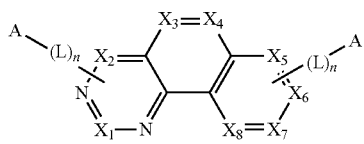

[Formula 7]

-continued

[Formula 8]

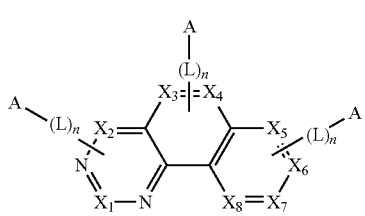

wherein L, $X_1$ to $X_8$, A, and n are as defined in Formula 1.

3. An organic electroluminescence device comprising a first electrode, a second electrode, and at least one organic layer interposed between the first and second electrodes wherein the organic layer comprises the organic light emitting compound of Formula 1 according to claim 1.

4. The organic electroluminescence device according to claim 3, wherein the organic layer comprises at least one layer selected from a hole injecting layer, a hole transport layer, a functional layer having functions of both hole injection and hole transport, a light emitting layer, an electron transport layer, an electron injecting layer, and a layer having functions of both electron transport and electron injection.

5. The organic electroluminescence device according to claim 3, wherein the organic layer interposed between the first and second electrodes comprises a light emitting layer.

6. The organic electroluminescence device according to claim 5, wherein the light emitting layer is composed of at least one host compound and at least one dopant compound and the host compound comprises the organic light emitting compound of Formula 1 according to claim 1.

7. The organic electroluminescence device according to claim 6, wherein the dopant compound comprises at least one compound selected from copper, boron, iridium, platinum, palladium, and ruthenium complexes.

8. The organic electroluminescence device according to claim 3, wherein the organic layer is formed in plurality and the organic layers are each independently formed by a monomolecular deposition or solution process.

9. The organic electroluminescence device according to claim 3, wherein the organic layer further comprises one or more organic red, green or blue light emitting layers to achieve white light emission.

10. The organic electroluminescence device according to claim 3, wherein the organic electroluminescence device is used in a system selected from flat panel displays, flexible displays, monochromatic flat panel lighting systems, white flat panel lighting systems, flexible monochromatic lighting systems, and flexible white lighting systems.

11. An organic light emitting compound represented by Formula 1:

[Formula 1]

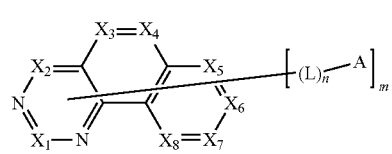

wherein A is selected from:

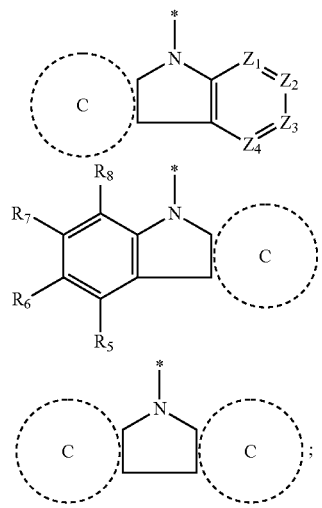

wherein $X_1$ to $X_8$ are identical to or different from each other and are each independently N or $CR_o$, provided that when $CR_o$ exists in plurality, the $CR_o$ groups are identical to or different from each other;

$Z_1$ to $Z_4$ are each independently N or are $CR_1$ to $CR_4$, respectively;

L represents a linker and is selected from the following structures:

[Structure B5]

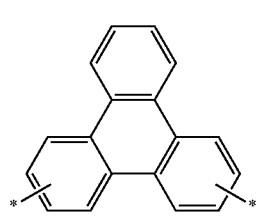

[Structure B6]

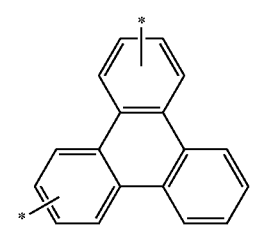

[Structure B7]

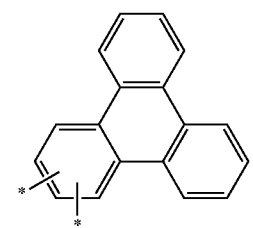

[Structure B8]

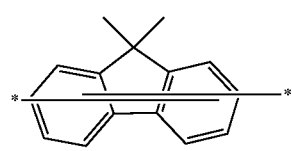

-continued

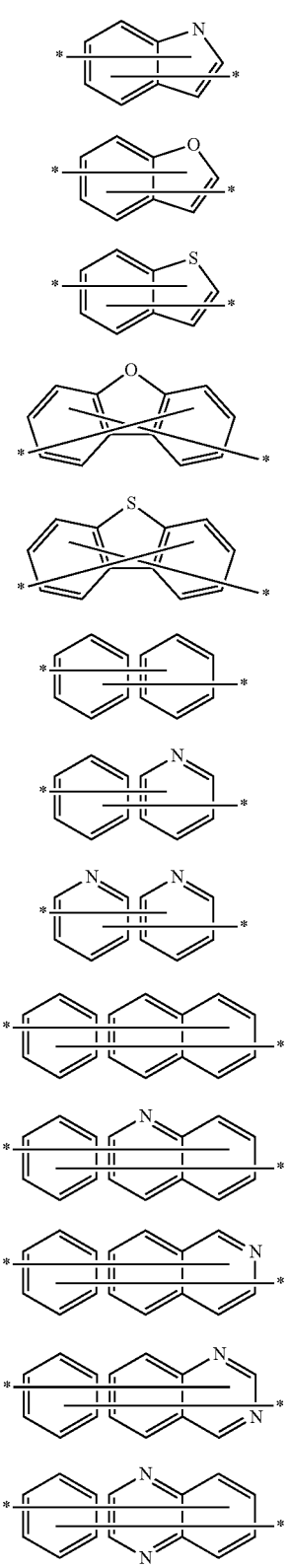

[Structure B9]
[Structure B10]
[Structure B11]
[Structure B13]
[Structure B14]
[Structure B18]
[Structure B19]
[Structure B20]
[Structure B21]
[Structure B22]
[Structure B23]
[Structure B24]
[Structure B25]

wherein hydrogen or deuterium atoms are optionally bonded to the carbon atoms of the aromatic rings and any one of $CR_o$ and $CR_1$ to $CR_8$ optionally replaces the nitrogen atoms;

n is an integer from 1 to 3, provided that when n is equal to or greater than 2, the plurality of L groups are identical to or different from each other;

$R_o$ and $R_1$ to $R_8$ are identical to or different from each other and are each independently selected from a hydrogen atom, a deuterium atom, substituted or unsubstituted $C_1$-$C_{30}$ alkyl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted $C_3$-$C_{60}$ cycloalkyl groups, substituted or unsubstituted $C_5$-$C_{30}$ cycloalkenyl groups, substituted or unsubstituted $C_5$-$C_{60}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_5$-$C_{60}$ arylthio groups, —$SiR_{11}R_{12}R_{13}$, and —$NR_{14}R_{15}$, $R_{11}$ to $R_{15}$ are identical to or different from each other and are each independently selected from a hydrogen atom, a deuterium atom, substituted or unsubstituted $C_1$-$C_{30}$ alkyl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted $C_3$-$C_{60}$ cycloalkyl groups, substituted or unsubstituted $C_5$-$C_{30}$ cycloalkenyl groups, substituted or unsubstituted $C_5$-$C_{60}$ aryloxy groups, substituted or unsubstituted $C_1$-$C_{30}$ alkylthioxy groups, substituted or unsubstituted $C_5$-$C_{30}$ arylthioxy groups, and substituted or unsubstituted $C_5$-$C_{60}$ arylthio groups, and m is an integer from 1 to 3;

wherein each

is selected from:

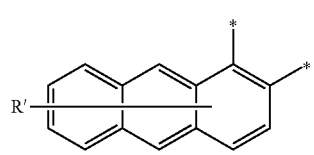

C3

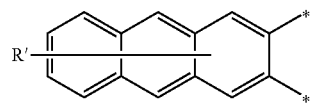

C4

C5 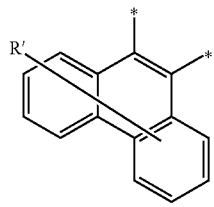

C6 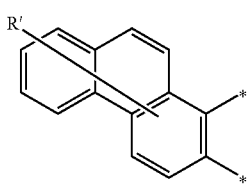

C7 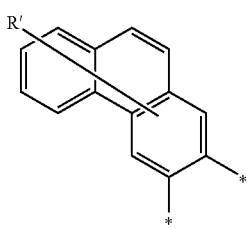

C8 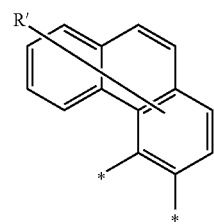

C9 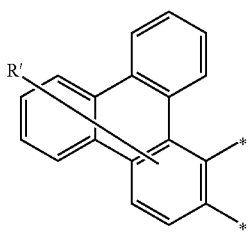

C10 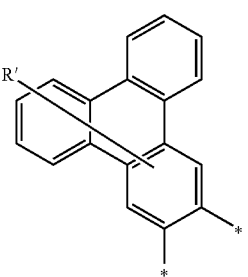

C11 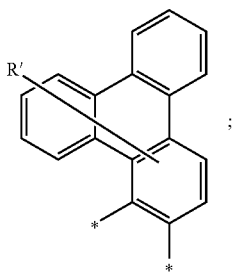

and
wherein each asterisk (*) represents a bonding site and each R' has the same meaning as $R_1$ to $R_8$.

12. An organic light emitting compound represented by Formula 1:

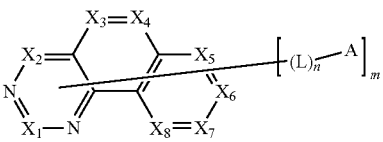 [Formula 1]

wherein A is:

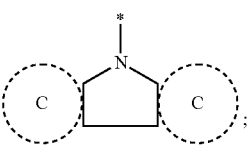

wherein $X_1$ to $X_8$ are identical to or different from each other and are each independently N or $CR_o$, provided that when $CR_o$ exists in plurality, the $CR_o$ groups are identical to or different from each other;

$Z_1$ to $Z_4$ are each independently N or are $CR_1$ to $CR_4$, respectively;

L represents a linker and is a single bond or is selected from the following structures:

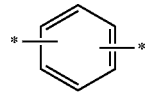 [Structure B1]

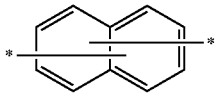 [Structure B2]

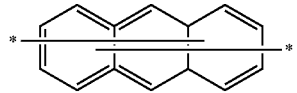 [Structure B3]

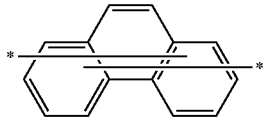 [Structure B4]

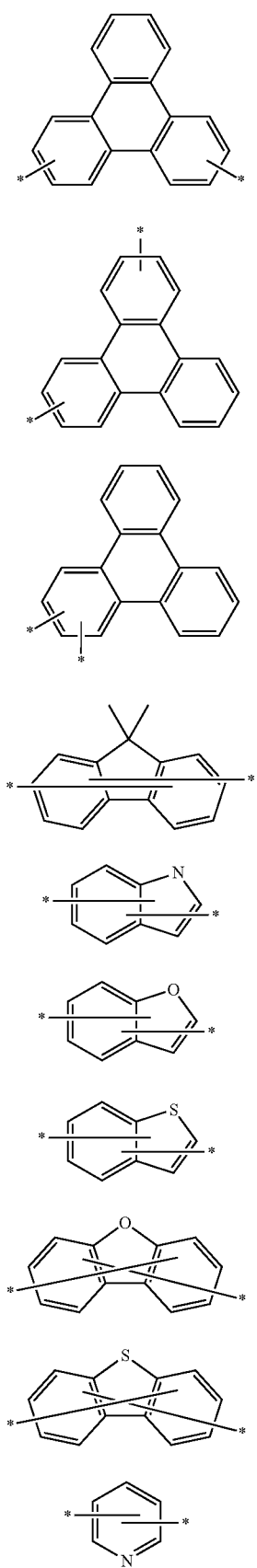

[Structure B5]

[Structure B6]

[Structure B7]

[Structure B8]

[Structure B9]

[Structure B10]

[Structure B11]

[Structure B13]

[Structure B14]

[Structure B15]

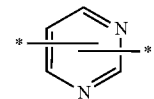

[Structure B16]

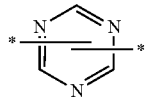

[Structure B17]

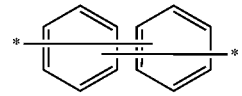

[Structure B18]

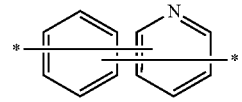

[Structure B19]

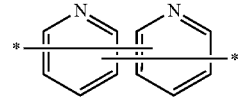

[Structure B20]

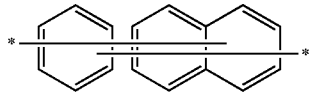

[Structure B21]

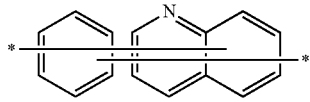

[Structure B22]

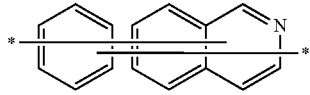

[Structure B23]

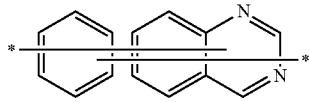

[Structure B24]

[Structure B25]

wherein hydrogen or deuterium atoms are optionally bonded to the carbon atoms of the aromatic rings and any one of $CR_o$ and $CR_1$ to $CR_8$ optionally replaces the nitrogen atoms;

n is an integer from 1 to 3, provided that when n is equal to or greater than 2, the plurality of L groups are identical to or different from each other;

$R_o$ and $R_1$ to $R_8$ are identical to or different from each other and are each independently selected from a hydrogen atom, a deuterium atom, substituted or unsubstituted $C_1$-$C_{30}$ alkyl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted $C_2$-$C_{60}$ alkenyl groups, substituted or unsubstituted $C_2$-$C_{60}$ alkynyl groups, substituted or unsubstituted $C_1$-$C_{60}$ alkoxy groups, substituted or unsubstituted C₃-C₆₀ cycloalkyl groups, substituted or unsubstituted C₅-C₃₀ cycloalkenyl groups, substituted or unsubstituted C₅-C₆₀ aryloxy groups, substituted or unsubstituted C₁-C₃₀ alkylthioxy groups, substituted or unsubstituted C₅-C₃₀ arylthioxy groups, substituted or unsubstituted C₅-C₆₀ arylthio groups, —SiR₁₁R₁₂R₁₃, and —NR₁₄R₁₅, R₁₁ to R₁₅ are identical to or different from each other and are each independently selected from a hydrogen atom, a deuterium atom, substituted or unsubstituted C₁-C₃₀ alkyl groups, halogen atoms, a hydroxyl group, a cyano group, a nitro group, an amino group, an amidino group, a hydrazino group, a hydrazono group, a carboxyl group or salts thereof, a sulfonic acid group or salts thereof, a phosphoric acid group or salts thereof, substituted or unsubstituted C₂-C₆₀ alkenyl groups, substituted or unsubstituted C₂-C₆₀ alkynyl groups, substituted or unsubstituted C₁-C₆₀ alkoxy groups, substituted or unsubstituted C₃-C₆₀ cycloalkyl groups, substituted or unsubstituted C₅-C₃₀ cycloalkenyl groups, substituted or unsubstituted C₅-C₆₀ aryloxy groups, substituted or unsubstituted C₁-C₃₀ alkylthioxy groups, substituted or unsubstituted C₅-C₃₀ arylthioxy groups, and substituted or unsubstituted C₅-C₆₀ arylthio groups, and m is an integer from 1 to 3;

wherein each

is selected from:

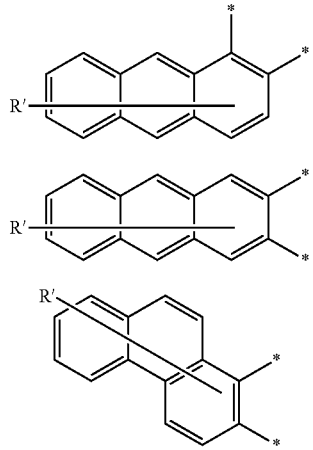

C3

C4

C6

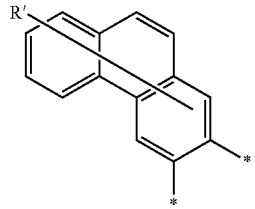

C7

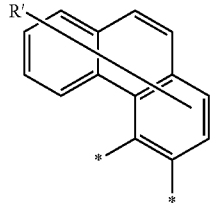

C8

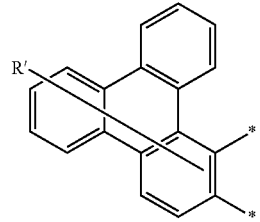

C9

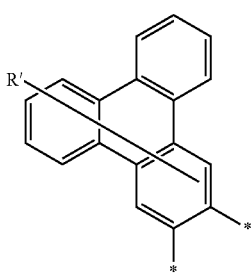

C10

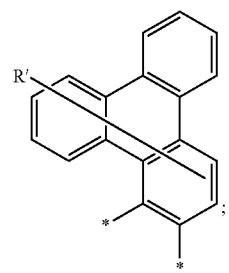

C11 and wherein each asterisk (*) represents a bonding site and each R' has the same meaning as R₁ to R₈.

* * * * *